United States Patent [19]

Takatsu et al.

[11] Patent Number: 5,453,491
[45] Date of Patent: Sep. 26, 1995

[54] MURINE INTERLEUKIN-5 RECEPTOR

[75] Inventors: Kiyoshi Takatsu, 301-32, Ishiharamachi, Kumamoto-shi, Kumamoto-ken, Japan; Akiro Tominaga; Satoshi Takagi, both of Kumamoto; Yoshiyuki Murata, Shimonoseki, all of Japan

[73] Assignee: Takatsu; Kiyoshi, Japan

[21] Appl. No.: 757,390

[22] Filed: Sep. 10, 1991

[30] Foreign Application Priority Data

Sep. 11, 1990 [JP] Japan .................................. 2-240638

[51] Int. Cl.$^6$ .............................. C12N 15/24; C07K 14/54
[52] U.S. Cl. ...................... 530/351; 536/23.52; 530/350; 530/395
[58] Field of Search ..................... 530/350, 351, 530/345

[56] References Cited

U.S. PATENT DOCUMENTS

| | | | |
|---|---|---|---|
| 4,859,609 | 8/1989 | Dull et al. | 436/501 |
| 5,006,459 | 4/1991 | Kuny et al. | 435/5 |

FOREIGN PATENT DOCUMENTS

| | | |
|---|---|---|
| 8928720 | 7/1989 | Australia . |
| 0325474 | 7/1989 | European Pat. Off. . |
| 0367566 | 5/1990 | European Pat. Off. . |
| WO-A-9007518 | 7/1990 | WIPO . |

OTHER PUBLICATIONS

Casman, *DNA and Protein Engineering Techniques* vol. 2(1), 1990, pp. 1–3.
Dower et al, *J. Clin. Immunol* 10(6) 1990, pp. 289–299.
Bozon, Immunol Today 11(10) 1990, pp. 350–354.
Takaki et al., Lymphokine Research 9:572, 1990.
Gearing et al., EMBO Journal 8:3667–3676, 1989.
Yamaguchi et al., International Immuno. 2:181–188, 1990.
Rolink et al., J. EXP. MED. 169:1693–1701, 1989.
Takaki et al., EMBO Journal 9:4367–4374, 1990.
Tavernier et al., Cell 66: 1175–1184, 1991.
Mita et al, PNAS 86, 1989, pp. 2311–2315.
Devas et al *EMBO* 10(8) 1991, pp. 2133–2137.
Devas et al, *Biochem Biophys Res. Comm* 172(2) 1990, pp. 570–575.
Kaczmaraski et al, *Blood Rev.* 5(3) 1991, pp. 193–203 (abst only).
Tavernier et al, *PNAS* 89, 1992, pp. 7041–7045.
Hitoshi et al, *J. Immunol.*, 144, 1990, pp. 4218–4225.

*Primary Examiner*—Marianne P. Allen
*Attorney, Agent, or Firm*—Pennie & Edmonds

[57] ABSTRACT

The invention provides an isolated cDNA sequence coding for murine interleukin 5 receptor, murine secretory interleukin 5 receptor, human interleukin 5 receptor, and human secretory interleukin 5 receptor and products including murine interleukin 5 receptor, murine secretory interleukin 5 receptor, and human interleukin 5 receptor which are produced using the isolated cDNA sequence. These products may be useful for a therapeutic agent for autoimmune disorders and diseases with eosinophilia in which human IL-5 is believed to be involved.

5 Claims, 10 Drawing Sheets

MURINE INTERLEUKIN-5 RECEPTOR

BACKGROUND OF THE INVENTION

1. Field of the Invention

The present invention relates to isolated cDNA sequences coding for murine interleukin 5 receptors, murine secretory interleukin 5 receptors and human interleukin 5 recepters and to murine interleukin 5 receptors, murine secretory interleukin 5 receptors and human interleukin 5 receptors which are produced using the isolated cDNA sequences as well as to methods of producing the interleukin 5 receptors.

2. Prior Art

Interleukin 5 (referred to as "IL-5", hereinafter) is a proliferation and differentiation factor for eosinophils and B lineage cells (Immunol. Rev. 102: 29, 107.,1988). It has been known that IL-5 is produced especially by T cells primed with *Mycobacterium tuberculosis,* parasites or alloantigens (J. Immunol. 140: 1175, 1988; Nature, 324: 70, 1986). IL-5 has also been known to induce production of IgM class immunoglobulin including anti-DNA antibody. Recently, IL-5 has been suspected of involvement in autoimmune diseases and there is a report that IL-5 is closely associated with eosinophilia accompanied by autoantibody production, fascitis and myositis (Eosinophils, Oxford University Press, 1988).

There are two types of IL-5 receptors (referred to as "IL-5R", hereinafter), namely, membrane bound IL-5R and secretory IL-5R. Among them, mouse secretory IL-5R is able to bind to human IL-5 and therefore expected to serve as a therapeutic agent for diseases associated with IL-5.

The inventors have obtained IL-5 responsive early B cells, T 88 and T-88M by culturing mouse bone marrow cells in the presence of IL-5 (Growth Factors 1: 135 1989) and produced IL-5R. The cross-linking reaction and subsequent SDS-PAGE analysis have revealed that IL-5R comprises at least two types of subunits, one having a molecular weight of about 46,500 and the other having a molecular weight of about 114,000, and that there are two types of IL-5R, a low affinity IL-5R having the dissociation constant of 27 nM and a high affinity IL-5R having the dissociation constant of 150 pM. It has been believed that the low affinity IL-5R comprises the small subunit of an estimated molecular weight of 46,500 while a high affinity IL-5R comprises the large subunit (MW: 114,000) and the small subunit (46,500) (Proc. Natl. Acad. Sci. USA 86: 2311, 1989).

The inventors have produced H7 and T21 monoclonal antibodies by immunizing rats with a membrane fraction of T88-M cells, which inhibit the binding of IL-5 to IL-5R (Int. Immunol. 2: 181, 1990; J. Immunol. 144: 4218, 1990). Anti-IL-5R antibodies, H7 and T21, are found to bind to glycoprotein of the molecular weight of about 60,000 according to the SDS-PAGE analysis. The real molecular weight of the small subunit is found to be about 55,000 according to the binding assay using IL-5 free of an oligosaccharide, suggesting that the low affinity IL-5R comprises a single molecule of molecular weight of about 60,000 (Int. Immunol. 2: 181, 1990).

We have also reported recently that IL-5R is found on the cell surface of human eosinophils. The dissociation constant of human IL-5R is 170–330 pM and the molecular weight is 55,000–60,000 according to the SDS-PAGE analysis. Human IL-5R appears to be comparable to a low affinity murine IL-5R (Migita, M., Yamaguchi, N., Mita, S., Higuchi, S., Hitoshi, Y., Yoshida, Y., Tomonaga, M., Matsuda, I., Tominaga, A., Takatsu, K., 1991, Cellular Immunology, 133: 484-497).

There has been no report on the isolation of a DNA sequence coding for the low affinity murine/human IL-5R. An object of the invention is to isolate the DNA sequence coding for the low affinity murine/human IL-5R and to determine the DNA sequence. The isolated DNA sequence may be used to produce murine/human IL-5R in mammalian cells. Another object of the invention is to obtain a DNA sequence coding for secretory IL-5R which is distinct from the DNA sequence coding for membrane bound IL-5R and to produce pure secretory IL-5R using the DNA.

The present invention is characterized by the following description:

(1). An isolated cDNA sequence coding for murine interleukin 5 receptor which is synthesized from murine early B cell mRNA.

(2). The isolated cDNA sequence of (1) wherein the nucleotide sequence comprises the open reading frame sequence described in SEQ ID No. 1.

(3) The isolated cDNA sequence of (1) wherein the nucleotide sequence comprises the entire sequence described in SEQ ID No. 2.

(4). An isolated cDNA sequence coding for secretory murine IL-5R which is synthesized from murine early B cell mRNA.

(5) The isolated cDNA sequence of (4) wherein the nucleotide sequence comprises the open reading frame sequence described in SEQ ID No. 3.

(6). The isolated cDNA sequence of (4) wherein the nucleotide sequence comprises the entire sequence described in SEQ ID No. 4.

(7). An isolated murine interleukin 5 receptor wherein the amino acid sequence comprises the sequence described in SEQ ID No. 5.

(8). An isolated murine interleukin 5 receptor wherein the amino acid sequence comprises the sequence described in SEQ ID No. 6.

(9) An isolated murine secretory interleukin 5 receptor wherein the amino acid sequence comprises the sequence described in SEQ ID No. 7.

(10) An isolated murine secretory interleukin 5 receptor wherein the amino acid sequence comprises the sequence described in SEQ ID No. 8.

(11). A method of producing the murine interleukin 5 receptors which comprises culturing cells capable of expressing the murine interleukin 5 receptors in medium and isolating the murine interleukin 5 receptors from the cells or the culture supernatant using anti-interleukin 5 receptor antibodies.

(12) A COS 7 monkey cell (ATCC CRL 1651) transfected with a recombinant vector containing the cDNA sequence of any one of (1)–(6).

(13) A method of producing the murine interleukin 5 receptors and the murine secretory interleukin 5 receptors comprises culturing the COS 7 cell transfected with relevant DNA in medium, and recovering the murine interleukin 5 receptors from the cells or secretory murine interleukin 5 receptors from the culture supernatant.

(14). An isolated cDNA sequence coding for human interleukin 5 receptor which is synthesized from mRNA of a human peripheral blood eosinophil.

(15). The isolated cDNA sequence of (14) wherein the nucleotide described in SEQ ID No. 9 comprises the open reading frame sequence coding for human interleukin 5 receptor.

(16). The isolated cDNA sequence of (14) wherein the nucleotide sequence described in SEQ ID No. 10 comprises the entire sequence coding for human interleukin 5 receptor.

(17). The isolated cDNA sequence of (14) wherein the nucleotide sequence described in SEQ ID No. 11 comprises the open reading frame sequence coding for human interleukin 5 receptor 2.

(18). The isolated cDNA sequence of (14) wherein the nucleotide sequence described in SEQ ID No. 12. comprises the entire sequence coding for human interleukin 5 receptor 2.

(19). An isolated human interleukin 5 receptor wherein the amino acid sequence comprises the sequence described in SEQ ID NO. 13.

(20). An isolated human interleukin 5 receptor wherein the amino acid sequence comprises the sequence described in SEQ ID NO. 14.

(21). The isolated cDNA sequence of (14) coding for a whole or part of amino acid residue numbers 1–333 described in SEQ ID No. 13

(22). A secretory human interleukin 5 receptor which lacks a cytoplasmic region and a transmembrane region of human interleukin 5 receptor.

(23). An expression vector comprising the cDNA sequence of any one of (14), (15), (16), (17), (18), and (21).

(24). A method of producing the secretory human interleukin 5 receptor and its analogues which comprises culturing a recombinant vector coding for the secretory human interleukin 5 receptor under the conditions which promote the expression thereof and recovering the secretory human interleukin 5 receptor.

SUMMARY OF THE INVENTION

The invention provides isolated DNA sequences coding for murine/human IL-5R and pure murine IL-5R produced by a genetic engineering technique using the isolated DNA sequence as well as an isolated DNA sequence coding for secretory murine IL-5R. The DNA sequence coding for secretory murine IL-5R is especially valuable in constructing a nucleotide sequence corresponding to the sequence of secretory human IL-5R and in producing secretory human IL-5R using the DNA sequence. The secretory human IL-5R thus produced may be utilized as a therapeutic agent for autoimmune disorders or diseases with eosinophilia in which IL-5 is believed to be involved and may greatly contribute to the medical and pharmaceutical field.

BRIEF DESCRIPTION OF THE DRAWINGS

The Invention is explained referring to the attached drawings.

DETAILED DESCRIPTION OF THE INVENTION

The description which relates to murine IL-5R is indicated (Murine) and which relates to human IL-5R is indicated (Human).

Preparation of Poly(A)$^+$RNA from Mouse Bone Marrow Cells (Murine)

In order to prepare the cDNA coding for the IL-5R, mRNAs are recovered from the mouse bone marrow cells having IL-5R. Mouse bone marrow cells are obtainable by a long-term bone marrow cell culture in the presence of IL-5 (Growth Factor 1: 135, 1989). A suitable source of cells may be a Balb/c mouse bone marrow long-term culture cell line, Y16, which is early B cells and shows a strong response to IL-5 (even at a concentration of 1 pg/ml of IL-5). RNA is prepared from the cell according to the method described by Okayama et al. (Methods in Enzymology 154: 3 1987). Poly(A)⁺RNA is recovered by fractionating the total RNA with the affinity chromatography using an oligo (dT) cellulose column.

Construction of cDNA Library from mRNA (Murine)

Figure 2A:
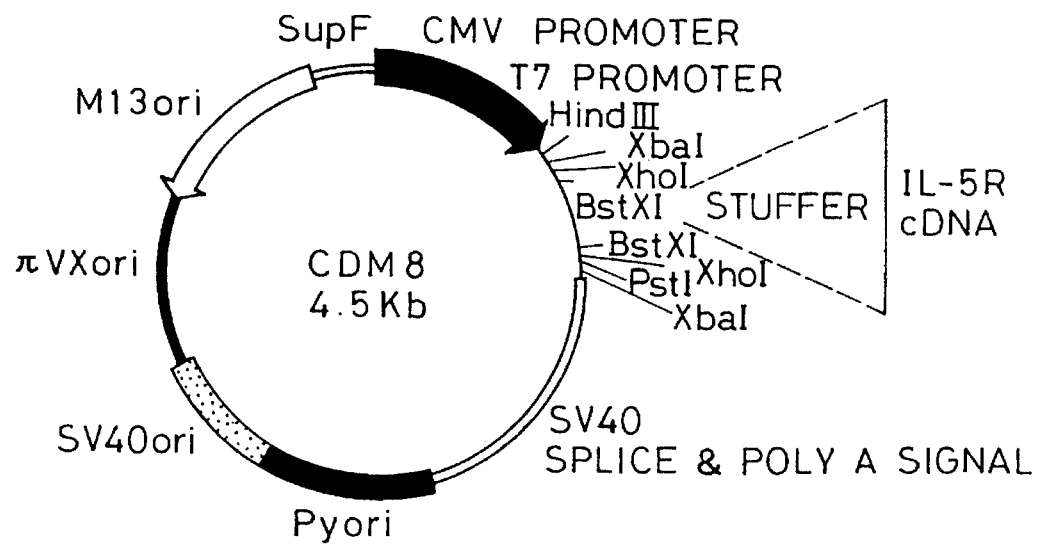
FIGS. 2A–2B shows vectors used in the present invention and a site of inserting an isolated DNA into the vector.

The poly(A)⁺RNA is reverse transcribed to cDNA using random primers and reverse transcriptase (Gene 25: 263, 1983). The cDNA larger than 1.0 kb is selected for cloning and inserted into the BstXI site of CDM 8 vector (see FIG. 2A) containing a cytomegalovirus promoter according to the method described by Seed et al. (Proc. Natl. Acad. Sci. USA 84: 8573, 1987). E. coli is transformed with the recombinant plasmid in order to provide cDNA library expressible in mammals.

Cloning of IL-5R Gene: Transfection of COS7 Cells Using the DNA of the Transformant (Murine)

COS 7 cells (Green monkey kidney cells) are transfected with the DNA according to the DEAE dextran or protoplast fusion method. The COS7 transformant is screened using anti-IL-5R antibodies H7 and T21 according to the method described by Seed et al. (Nature 329: 840, 1988). H7 and T21 antibodies and the COS7 suspension are incubated together. After incubation, the mixture is transferred to plates coated with goat anti-rat IgG antibody (H7 and T21 are rat IgG antibodies). Then, plasmid DNA is recovered from the COS7 cells immobilized on the bottom of the plate. The transformation-screening procedure described above is repeated several times. After screening, a group of the selected COS7 transformant is further screened by flow cytometry using fluorescein-conjugated H7 and T21 and the transformant containing IL-5R cDNA is identified.

The Entire Structure of murine IL-5R Genes (Murine)

Figure 1:
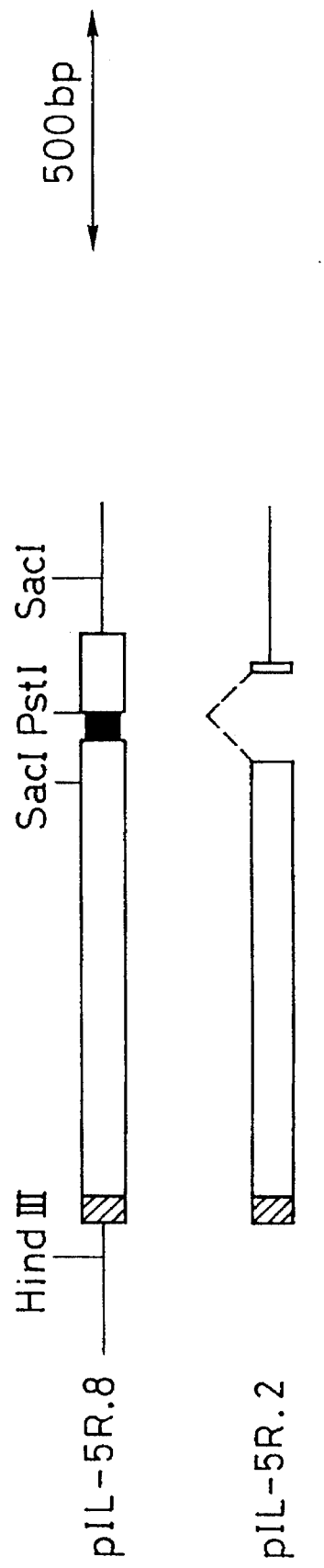
FIG. 1 shows partial restriction maps of two IL-5R cDNA clones. The box indicates an open reading frame which is expected to be translated. The shaded portion at the 5'-end indicates a signal peptide, and the solid portion indicates the transmembrane region.

The rough restriction maps of IL-5R cDNA isolated above are shown in FIG. 1. pIL-5R.8 is the cDNA clone prepared first from the CDM 8 library. pIL-5R.2 is obtained from the cDNA library using the HindIII-PstI fragment of pIL-5R.8 as a probe according to the colony hybridization method.

The nucleotide sequences of the cDNA fragments of pIL-5R.2 and pIL-5R.8 are determined according to the method described by Sanger et al (Proc. Natl. Acad. Sci. USA 74: 5463, 1977). The entire nucleotide sequence of the cDNA fragment of pIL-5R.8 and the deduced amino acid sequence are shown in SEQ ID No. 15. The nucleotide A of the ATG initiation codon is numbered 303 and the amino acid methionine is numbered 1. The cDNA fragment of pIL-5R.8 has 1808 nucleotides in length which codes for 415 amino acids. This polypeptide consists of 4 portions according to Hydropathy plot (OF URFS and ORFS, Rusell F, Doolittle, University Science Books, 1987): singal peptide (See amino acids 1–17 of SEQ ID NO: 15), extracellular region, transmembrane region, and cytoplasmic region. The amino acids at positions 32–34, 128–130, 213–215, 241–243, 392–394, and 412–414 of SEQ ID NO. 15 are presumably linked to N-linked oligosaccharide. pIL-5R.2 lacks a transmembrane region (FIG. 1 and SEQ ID No. 16) and therefore, IL-5R expressed by pIL-5R.2 is a secretory type. As shown in SEQ ID No. 16, pIL-5R.2 lacks the sequence between the nucleotide Nos. 986 and 1164

Expression of IL-5R gene (Murine)

Figure 2B:
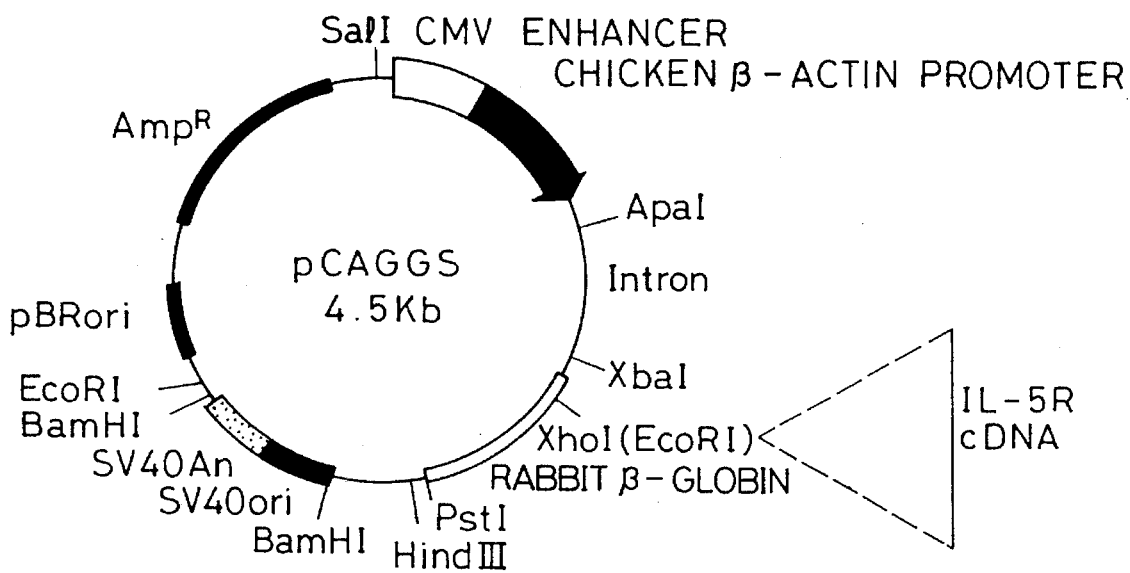

The following two types of vectors, CDM8 and pCAGGS, can be utilized as expression vectors for an isolated IL-5R cDNA sequence (see FIG. 2).

CDM 8 vector: The vector demonstrates an elevated DNA expression in mammalian cells. The vector has two BstXI sites. The vector is digested with BstXI and both ends of cDNA of interest are ligated to a BstXI linker. The cDNA-linker complex is ligated to the BstXI digested vector.

pCAGGS vector: The vector contains a CMV enhancer upstream of the promoter of pAGS-3, which is a vector having a much stronger expression ability than that of CDM8 (Gene, 79:269, 1989). The cDNA insertion site of pCAGGS is XhoI site substituted with EcoRI site in the exon of rabit β-globin gene region. The pCAGGS vector demonstrate a higher level of DNA product expression than pAGS-3.

In the Example of the invention, the pCAGGS vector is used for expression test of IL-5R and the expressed murine IL-5R is tested by IL-5 binding test, IL-5 cross-linking test and immunoprecipitation test using monoclonal antibody, H7.

The murine IL-5R cDNA encoding a secretory IL-5R is inserted into the XhoI (EcoRI) site of the pCAGGS vector. COS7 (Green monkey kidney cell, ATCC CRL1651 ) is transfected with the recombinant plasmid and the resulting transformant is grown in a medium. The amino acid sequence of the peptide in the culture supernatant is determined. The N-terminal 20 amino acids thus determined are the same as those deduced from the nucleotide sequence of the murine IL-5R cDNA. The COS7 culture supernatant containing soluble IL-5R inhibits the binding of IL-5 to IL-5R expressed on B cells or eosinophils.

Binding Assay of IL-5R to IL-5 (Murine)

The COS7 transformant thus obtained is tested for the production of IL-5R capable of binding to IL-5 using ³⁵S-methionine and ³⁵S-cysteine labeled IL-5 (J. Immunol. 140: 1175, 1988; J. Exp. Med. 168: 863, 1988). Binding of the labeled IL-5 is inhibited by the excess amount (100-fold) of the non-labelled IL-5 and thus the cDNA clone pIL-5R.8 is confirmed to code for IL-5R.

Cross-linking of IL-5R to IL-5 and Immunoprecipitation of IL-5R to IL-5 (Murine)

COS7 cells are transfected with pIL-5R.8 followed by cross-linking reaction and immunoprecipitation.

Cross-linking: IL-5R produced by the transformant is tested whether it is the same as those expressed by a IL-5 responsive early B cell, T88-M, by the cross-linking test using ³⁵S-labeled IL-5 (Proc. Natl. Acad. Sci. USA, 1989, 86: 2311). After electrophoresis, the band pattern on the gel indicates that the molecular weight comparable to IL-5 monomer is decreased (about 22,000) under reduced condition.

Immunoprecipitation: The surface proteins of the transfected cells is ¹²⁵I-labeled and immunoprecipitated with anti-IL-5R antibodies, H7 (Int. Immunol. 2: 181, 1990). IL-5R produced by the transformant is found to have a molecular weight of 60,000.

Cell Lines Expressing IL-5R mRNA and the Size of the IL-5R mRNA (Murine)

Poly(A)⁺RNA are prepared from IL-5 responsive cell lines such as Y16 (early-B cell), BCL1-B20 (mouse B cell chronic leukemia lymphoma, in vitro line), mouse myeloma cell, MOPC104E, X5568, L cell, IL-3 responsive cell line FDC-P1 derived from mouse bone marrow long-term cultured cell, and IL-2 responsive mouse T cell lines. 2 μg of each of poly(A)⁺RNA are tested for the presence of IL-5R mRNA by Northern blot.

Northern blot is carried out using the HindIII-PstI fragment of pIL-5R.8 as a probe (Biochemistry 16:4743, 1977). IL-5 responsive cell lines including Y16, BCL1-B20, MOPC104E are found to express IL-5R mRNA with the size of 5–5.8 kb Preparation of Poly(A)⁺RNA from Human Peripheral Blood Eosinophils (Human)

A DNA sequence coding for human IL-5R is prepared from human peripheral blood eosinophils. Eosinophils are isolated from peripheral blood of healthy volunteers and of a patient with eosinophilia by a density gradient centrifugation using Ficoll (Migita, Y., et al. supra). Whole mRNA is prepared from eosinophils according to the method described by Okayama et al. (ibid). Poly(A)+ RNA is recovered by fractionating the whole RNA with the affinity chromatography using an oligo (dT) cellulose column. One of the poly(A)+RNA preparation is derived from healthy volunteers and the other is derived from a patient with eosinophilia.

Construction of cDNA Library from mRNA (Human)

The poly(A)+RNA is reverse transcribed to cDNA using random primers and reverse transcriptase as described above. The cDNA of more than 1.0 kb fragments is selected for cloning. The cDNA fragment derived from eosinophils of healthy volunteers (helv-cDNA) is inserted into the BstXI site of vector pAGS-3 (Miyazaki, et al., 1989, Gene, 79: 269) according to the method described by Seed et al. (ibid). *E. coli* is then transformed with the recombinant plasmid (helv-cDNA library). The cDNA derived from eosinophils of patients with eosinophilia (eosi-cDNA) is inserted into the EcoRI site of phage λgt10 using an EcoRI linker. *E. coli* is then infected with the recombinant phage (eosi-cDNA library).

Screening of Helv-cDNA and eosi-cDNA Libraries for Human IL-5R (Human)

The helv-cDNA library is screened using the HindIII-PstI fragment of pIL-5R.8. A positive clone is isolated and is designated as ph5R. 1. ph5R.1 lacks some of the nucleotide sequence of IL-5R. Subsequently, the eosi-cDNA library is screened using the nucleotide sequence of ph5R.1. Two positive clones designated as HSIL5R and HSIL5R2 are isolated.

Human IL-5R Gene Structure (Human)

Figure 6:
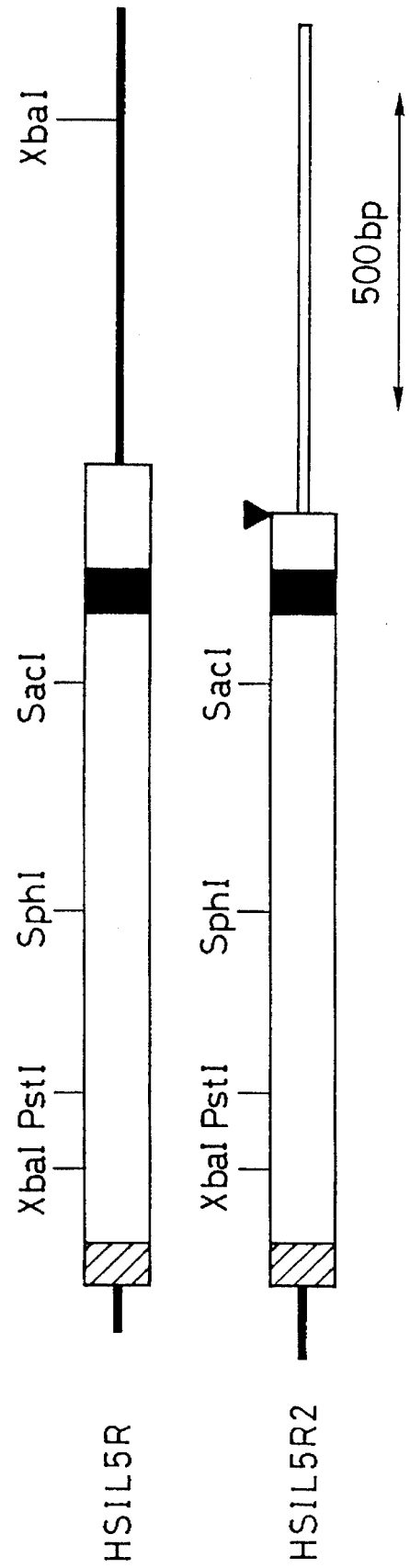
FIG. 6 shows a restriction map of a human IL-5R cDNA fragment of HSIL5R and HSIL5R2. The box represents the open reading frame of IL-5R. The 5' end hatched box is a putative signal peptide and the solid box is the predicted transmembrane region. The mark ▼ indicates the starting point of the nucleotide sequence which distinguishes HSIL5R from HSIL5R2.

FIG. 6 shows restriction maps of the isolated IL-5R cDNAs of HSIL5R and HSIL5R2. The nucleotide sequence was determined according to the Sanger's method (ibid). HSIL5R and HSIL5R2 are membrane bound receptors. The cytoplasmic domain sequence of HSIL5R2 is shorter than that of HSIL5R.

SEQ ID No. 17 and No. 18 show the nucleotiode and deduced amino acid sequence of HSIL5R (420 amino acids in length) and HSIL5R2 (396 amino acid in length), respectively. The amino acid sequence is analyzed as described above.

HSIL5R and HSIL5R2 consist of signal peptide region, extracellular region, transmembrane region, cytoplasmic region. The nucleotide sequence downstream of nucleotide position 1245 distinguishes HSIL5R (SEQ ID No. 17) from HSIL5R2 (SEQ ID No. 18). The amino acid sequence of HSIL5R2 terminates after amino acid Ile (amino acid number 396) located immediately after the nucleotide position 1245.

Expression of Human IL-5R (Human)

Human IL-5R cDNA is inserted into a pCAGGS vector, and COS 7 cells are transfected with the recombinant plasmid. λgt10 cDNA clones, HSIL5R and HSIL5R2 are digested with EcoRI and the IL-5R cDNA fragment is inserted into the EcoRI site of pCAGGS.

Binding Assay of transfectants with HSIL5R or HSIL5R2 to IL-5 (Human)

The IL-5R expression of the clones are tested using $^{35}$S-methionine- and $^{35}$S-cysteine-labeled murine IL-5 or $^{125}$I-labeled human IL-5. The human IL-5 is prepared as follows:

The IL-5 cDNA fragment is inserted into an expression vector derived from baculovirus. Sf21 cells (*Spodotera frugiperda*) are infected with the recombinant DNA. The cell are cultured and the culture supernatant is tested for human IL-5 using anti-IL-5 monoclonal antibody, NC17 (Proc. Natl. Acad. Sci. U.S.A. 84: 4581, 1987). The isolated human IL-5 is labeled with $^{125}$I. Binding assay is carried out as described for murine IL-5R Cross-linking of IL-5R to IL-5 (Human)

IL-5R produced by the positive clones is tested whether it is the same as those produced by eosinophils, by cross-linking test using $^{35}$S-labeled murine IL-5 and $^{125}$I-labeled human IL-5 as described above.

Cell Lines Expressing IL-5R mRNA and the Size of the IL-5R mRNA (Human)

Poly(A)+RNA may be prepared from human eosinophils, erythroleukemic cell line TF-1, eosinophilic leukemia cell line EoL-3, ATL-2 adult T cell leukemia cell line ATL-2, Burkitt's lymphoma cell line Raji, and histiocytic lymphoma cell line U-937. 6 μg of each of poly(A)+ RNA is tested for the presence of IL-5R mRNA using the entire sequence of HSIL5R cDNA as a probe. Human eosinophils and TF-1cell line are found to express IL-5R mRNA with the size of 1.4 kb and 5.3 kb.

Production of Secretory Human IL-5R

HSIL5R cDNA is inserted into the EcoRI site of Bluescript SK(–). The construct is digested with SalI and KpnI. The SalI-KpnI digested fragment is then incubated with exonuclease III so that the sequence coding for the cytoplasmic domain and transmembrane domain of human IL-5R can be removed. The digested fragment is blunted with mung bean exonuclease followed by a treatment with a klenow fragment and subjected to ligation (Gene 33: 103, 1985). After treatment, a clone is obtained which contains deletion from 3' end to the nucleotide number 995 (SEQ ID No. 17), a site which corresponds to the starting point of deletion in the secretory murine IL-5R cDNA. The deletion mutant is digested with EcoRI and BssHII. The resulting DNA fragment is ligated to a linker containing a stop codon. After ligation, a DNA-linker complex is inserted into an appropriate restriction site of any vector. Alternatively, the HSIL-5R cDNA fragment of the Bluescript SK(–) construct is deleted from 3' end to the nucleotide number 996. As a result of frameshift, the construct contains two stop codons. The secretory human IL-5R construct thus obtained lacks DNA sequences for a cytoplasmic domain and a transmembrane domain and codes for 333 amino acids.

The secretory human IL-5R construct is introduced into host cells and the transfectant produces a secretory human IL-5R. An expression vector is selected according to host cells to be transfected. Host cells include prokaryotes such as gram negative bacteria (*E. coli*) or gram positive bacteria (Bacillus), yeast, and eukaryotic cell lines derived from insects and mammals.

EXAMPLES

The following Examples are described for murine secretory IL-5R and membrane type IL-5R.

Preparation of Polyadenylated RNA from Y16 Cell (Murine)

Y16 ($2 \times 10^7$) cells were placed in a 3 liter Spinner culture bottle containing a medium (RPMI 1640, 4% FCS, $5 \times 10^{-5}$M 2-mercaptoethanol,100 U/ml of penicillin, 100 μg/ml of streptomycin) and 300 pg/ml of IL-5. The bottle was sealed and incubated for a week. After incubation, about $5 \times 10^9$ cells were harvested. $1 \times 10^9$ cells were solubilized in 50 ml of 5.5M guanidium thiocyanate solution (pH 7.0) containing 25 mM sodium citrate, 0.5% sodium laurylsulcosine, and 0.2M 2-mercaptoethanol according to the method described by Okayama et al. (supra). The cell lysate was layered onto cesium trifluoroacetic acid solution (density: 1.5 g/ml) containing 0.1M EDTA/pH 7.0. The mixture was centrifuged at 15° C., at 125,000 g, for 24 hours. After centrifugation, the RNA pellet was dissolved in distilled water containning 10 mM Tris-HCl/pH 7.5 and 1 mM EDTA. The RNA solution was loaded onto an oligo (dT) cellulose column and the pass-through was loaded onto the column again (Molecular Cloning, 1989, Chapter 7, p 26, Cold Spring Harbor Laboratory Press). The oligo (dT) bounded fraction was eluted and 30 μg of poly(A)$^+$RNA was recovered.

Construction of cDNA Library in CDM8 (Murine)

30 μg of the poly(A)$^+$RNA thus obtained was used to synthesize cDNA using a cDNA synthesis kit (BRL, Bethesda, Md.) according to the method described by Seed (supra). The CDM8 vector (see FIG. 2A) was digested with BstXI. After digestion, an approximately 4100 bp fragment was purified by a potassium acetate density gradient centrifugation. The cDNA was ligated to a BstXI linker and a cDNA-linker complex containing cDNA having a size of 1,000 bp or more was selected by a potassium acetate density gradient centrifugation. The fractionated fragments were subjected to ligation with the purified CDM8 vector. E. coli MC1061/P3 was transformed with the construct and about 2 million transformants were obtained as a cDNA library.

Screening of the cDNA Library (Murine)

COS7 ($5\times10^5$) cells were placed in each of 100 plates (6 cm). The following day, the COS7 cell was transfected with 2 μg of the plasmid DNA (per plate) prepared from the cDNA library according to the DEAE-dextran method. On day 3, the COS7 cells were removed from the plates and incubated with antibodies, H7 and T21. The COS7 cell was screened for the presence of the H7 and T21 antigens using goat anti-rat IgG antibodies (Panning technique). After screening, plasmid DNAs were prepared from the H7 and T21 antigen positive COS7 cells. Then, E. coli MC106 1/P3 was transformed with the plasmid DNAs. Fresh COS7 cells were fused with the transformants according to the protoplast fusion method. The COS7 cells were screened for the presence of the H7 and T21 antigens according to the Panning technique. After four cycles of the procedure described above, fresh COS7 cells were transformed and the transformant was screened by the Panning technique using goat anti-rat IgG antibody F(ab')$_2$ fragment. This transformation-screening procedure was repeated two times in order to eliminate the contamination of Fc receptor genes. After screening, 50 independent colonies were selected and the plasmid DNA was prepared. Fresh COS7 cells were then transfected with the plasmid DNA and the transformants were tested for the presence of the H7 and T21 antigens. One of the transformants was found to be antigen positive and designated as pIL-5R.8.

The cDNA library prepared from Y16 as described above was screened for the presence of IL-5R cDNA using the fragment inserted in pIL-5R.8 as a probe according to the colony hybridization method (Molecular Cloning, 1989, chapter 1, p90, Cold Spring Harbor Laboratory Press): The HindIII-PstI fragment was prepared from pIL-5R.8 and radiolabeled with α-$^{32}$P-dCTP according to the random primer method. The transformants of the cDNA library were grown on a solid LB agarose medium (approximately 10,000 colonies per 10 cm plate) overnight. The colonies were transferred to a nitrocellulose membrane and the DNAs on the membrane were hybridized to the radiolabeled prove. Positive colonies were identified through autoradiography. One of the transformants was isolated and designated as pIL-5R.2.

Nucleotide Sequencing of IL-5R (Murine)

The cDNA fragment of pIL-5R.8 was digested with XbaI and inserted into a M13mp19 vector. The construct was digested with BamHI and KpnI. The BamHI-KpnI digested fragment was then digested with exonuclease III: the fragment was digested up to ten minutes with stopping digestion every minute. The digested fragment was blunted with mungbean exonuclease followed by a treatment with a klenow fragment and subjected to ligation (Gene 33:103, 1985). E. coli JM109 was transformed with the constructs to produce different sizes of the M13 deletion mutants. Single-stranded DNAs were prepared from the mutants (Methods in Enzymology 101:58, 1983) and the nucleotide sequence was determined using the M13 primer, 5'-GTTTTCCCAGT-CACGAC-3' according to the Sanger's method. Single-stranded DNA was also prepared from the M13 mutant containing the cDNA fragment of a reversed orientation and the nucleotide sequence was determined as described above. The nucleotide sequence thus obtained from the M13 mutant containing the cDNA fragment of a right orientation was found to be complementary to the one of M13 mutant containing the cDNA fragment of a reversed orientation.

SEQ ID No. 15 shows the complete nucleotide and amino acid sequence of pIL-5R.8. The first 17 amino acids are believed to be the signal peptide (Nucleic. Acids. Res. 14:4683, 1986) and the amino acids from amino acid position 340 to amino acid position 361 are considered to be the transmembrane region according to the hydropathy plot. Amino acids 32–34, 128–130, 213–215, 241–243, 392–394, and 412–414 appear to be sites of N-linked oligosaccharide addition. The previously estimated molecule weight (45, 284) of IL-5R differs from the real molecular weight (about 60,000) of IL-5R produced by the COS7 cells transfected with pIL-5.8. The difference of the weight may be due to the addition of N-linked oligosacharide. Nucleotide position 1467 represents the beginning of the deleted nucleotide sequence of pIL-5R.2 The nucleotide sequence of pIL-5R.2 shown in SEQ ID No. 16 was determined using primers(17-mers) synthesized based on the nucleotide sequence of pIL-5R.8, a T7 primer (5'-ATGGAAATTAATACG-3'), and a primer for the 3' end of CDM8 (5'-TGCAGGCGCA-GAACTGG-3') according to the Sanger's method. The pIL-5R.2 is a frame shift mutant, resulting in translation termination to give 4 peptides. The polypeptide encoded by pIL-5R.2 is a secretory IL-5R which is likely to act on B cells or eosinophils in the process of differentiation.

Expression and Binding Test of IL-5R cDNA (Murine)

pIL-5R.8 (CDM8 vector) was digested with XhoI and the IL-5R cDNA fragment was inserted into the XhoI site of pCAGGS vector (see FIG. 2B) whose EcoRI site had been replaced with a XhoI site.

The new construct was designated as pCAGGS.5R. 8. E. coli was transformed with the construct and the transformant was designated as E. coli 5R.8. E. coli 5R.8 was deposited with Fermentation Research Institute, Agency of Industrial Science and Technology and was assigned the accession number FERM BP 3085.

COS7 cells were transfected with pIL-5R.8 or pCAGGS.5R.8 and the cells were harvested two days later. 2-10×10$^4$ cells were incubated with different concentrations of $^{35}$S-labeled IL-5 (2.5×10$^8$ cpm/μg) in the presence or absence of 100-fold excess of non-labeled IL-5 at 37° C. for 10 minutes. After incubation, the number of IL-5 binding per cell was counted and the dissociation constant was calculated.

Figure 3A:
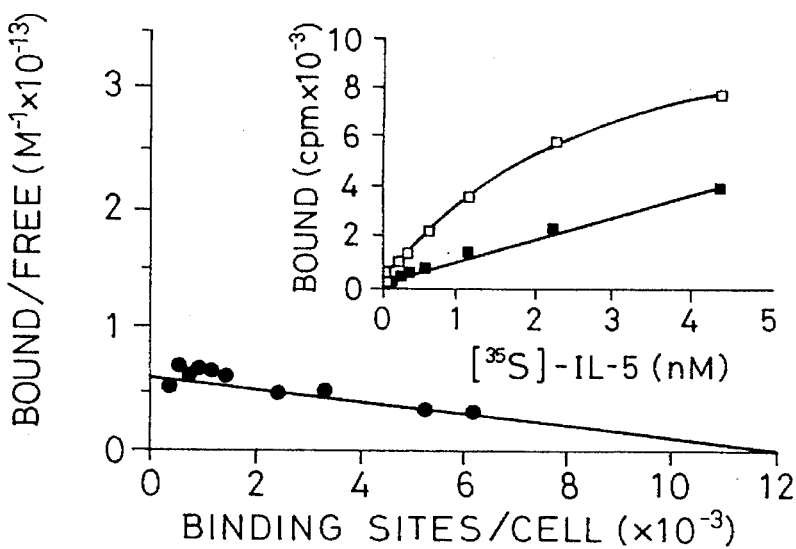
FIGS. 3A–3C shows the results of binding assay using $^{35}$S-labeled IL-5 and the Scatchard plot analysis.
Figure 3B:
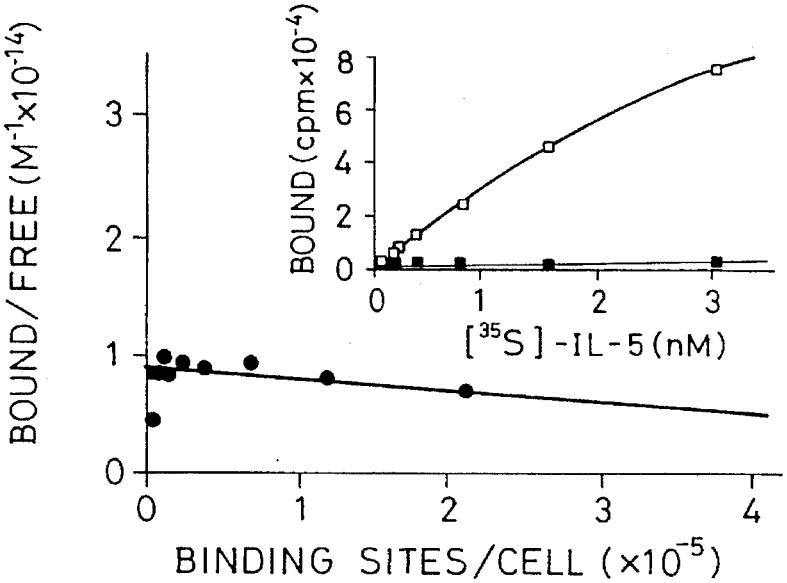
Figure 3C:
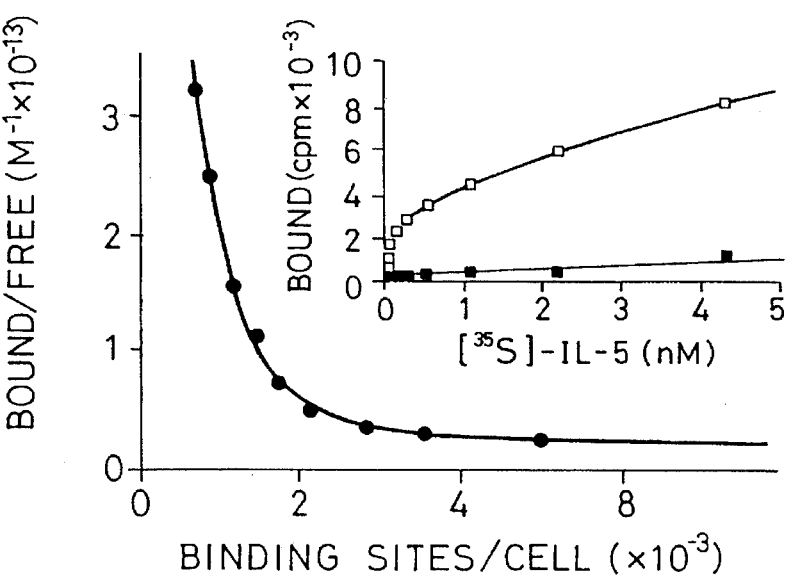

FIGS. 3(A), (B), (C) shows the Scatchard plot analysis (Ann N.Y. Acad. Sci, 51: 660, 1949) of $^{35}$S-labeled IL-5 binding to IL-5R expressed on transfectants and Y16 cells. The inset shows the direct binding data (□: total binding, ■: non-specific binding). FIG. 3(A) shows the results when COS7 cells were transfected with pIL-5R.8: the dissociation constant was 2 nM and the number of the IL-5 binding was 12,000/cell. FIG. 3(B) shows the results when COS7 cells were transfected with pCAGGS.5R.8: the dissociation constant was 9.6 nM and the number of the IL-5 binding was 880,000/cell. FIG. 3(C) shows the results when Y16 cells were also tested for the IL-5 binding. A high affinity IL-5R and a low affinity IL-5R were found in the Y16 cells. The high affinity IL-5R has the number of IL-5 binding of 1,200/cell with the dissociation constant (KD) of 20 pM. The low affinity IL-5R has the number of IL-5 binding of 22,000/cell with the dissociation constant (KD) of 5.1 nM. These results suggest that the inserted IL-5R cDNA encodes a low affinity IL-5 recepter.

Cross-linking Test of Low Affinity IL-5R to IL-5 (Murine)

Because COS7 cells transfected with pCAGGS.5R.8 were found to express IL-5R at a higher level than those transfected with pIL-5R.8, pCAGGS.5R.8 was used for the following experiments.

COS7 cells ($1\times10^5$) were transfected with pCAGGS or pCAGGS5R.8 and the transformants were incubated with 4 nM $^{35}$S-labeled IL-5 in the presence or absence of 100-fold excess of non-labeled IL-5 as follows: a pCAGGS transformant without non-labeled IL-5 (lane 1), a pCAGGS transformant with non-labeled IL-5 (lane 2), a pCAGGSSR.8 transformant without non-labeled IL-5 (lane 3, 5), a pCAGGS5R.8 transformant with non-labeled IL-5 (lane 4, 6). The mixture was incubated at 37° C. for 10 minutes. Cells were washed extensively and then disuccinimidyl tartarate (DST)(Piece Chemical, Rockford, Ill.) was added to the cell suspension. The cell suspension was incubated at 4° C. for 30 minutes and then 1% Triton X-100 was added to the suspension to disrupt the cells. The disrupted cell suspension was loaded on a 7.5% SDS-polyacrylamide gel in the reducing (lane 5, 6) or non-reducing (lane 1-4) conditions.

Figure 4:
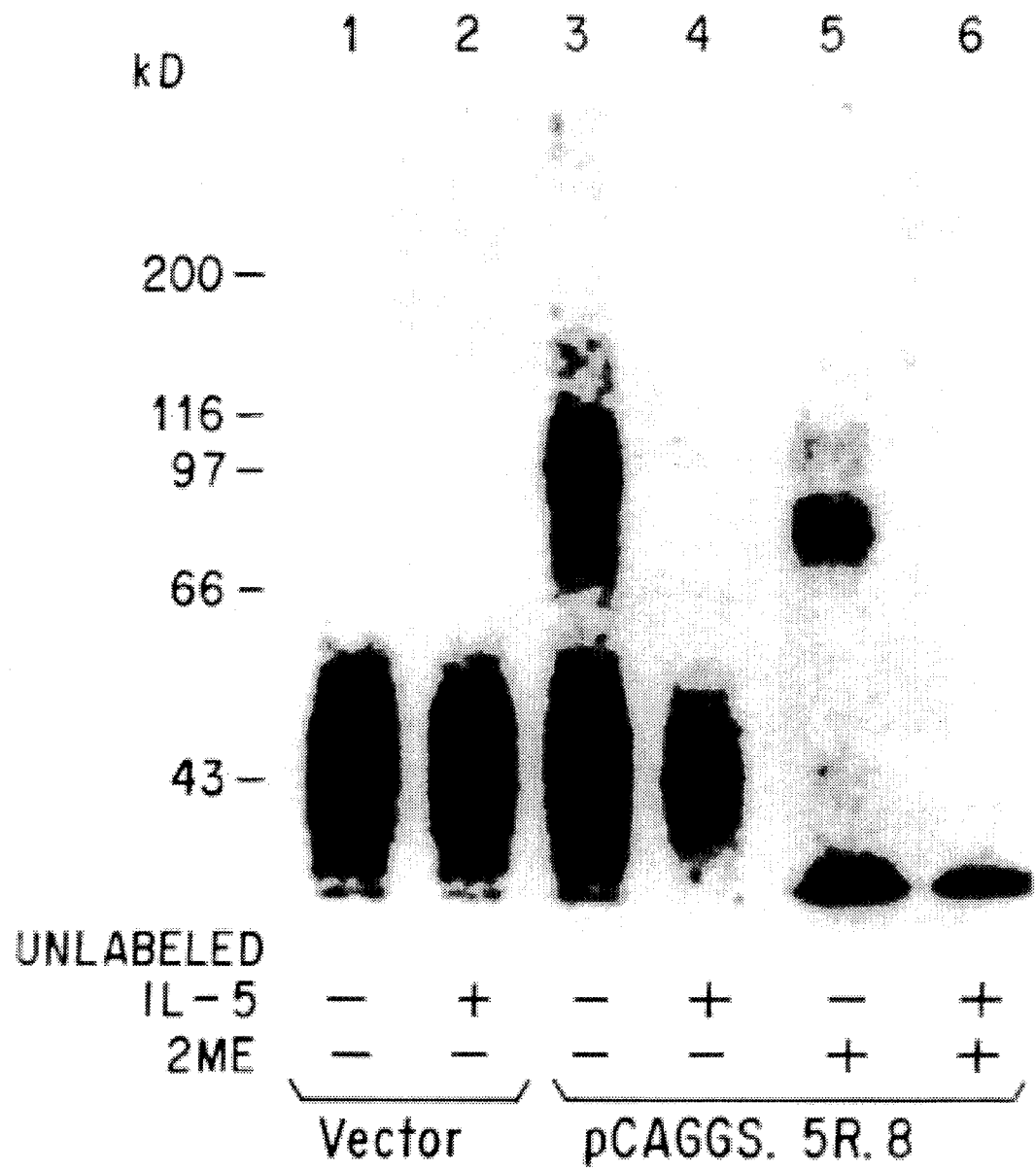
FIG. 4 shows the results of cross-linking experiment using $^{35}$S-labeled IL-5.

After electrophoresis, the gel was analyzed with Bio-Analyzer 100 (Fuji Film). The results are shown in FIG. 4. A band of approximately 90–100 KD in size was found which could be a low affinity IL-5R previously reported by Mita, et al., in Proc. Natl. Acad. Sci. U.S.A. 86: 2311, 1989. In contrast, the molecular weight of the band in the reducing condition was about 75 KD (lane 5 in FIG. 4). The difference was due to the dissociation of monomeric $^{35}$S-labeled IL-5 (MW: 22,000) from the IL-5-IL-5R complex, because biologically active IL-5 binds to its receptor as a disulfide-linked dimer.

Immunoprecipitation of IL-5R expressed on pCAGGS.5R.8 Transfected COS7 (Murine)

Figure 5:
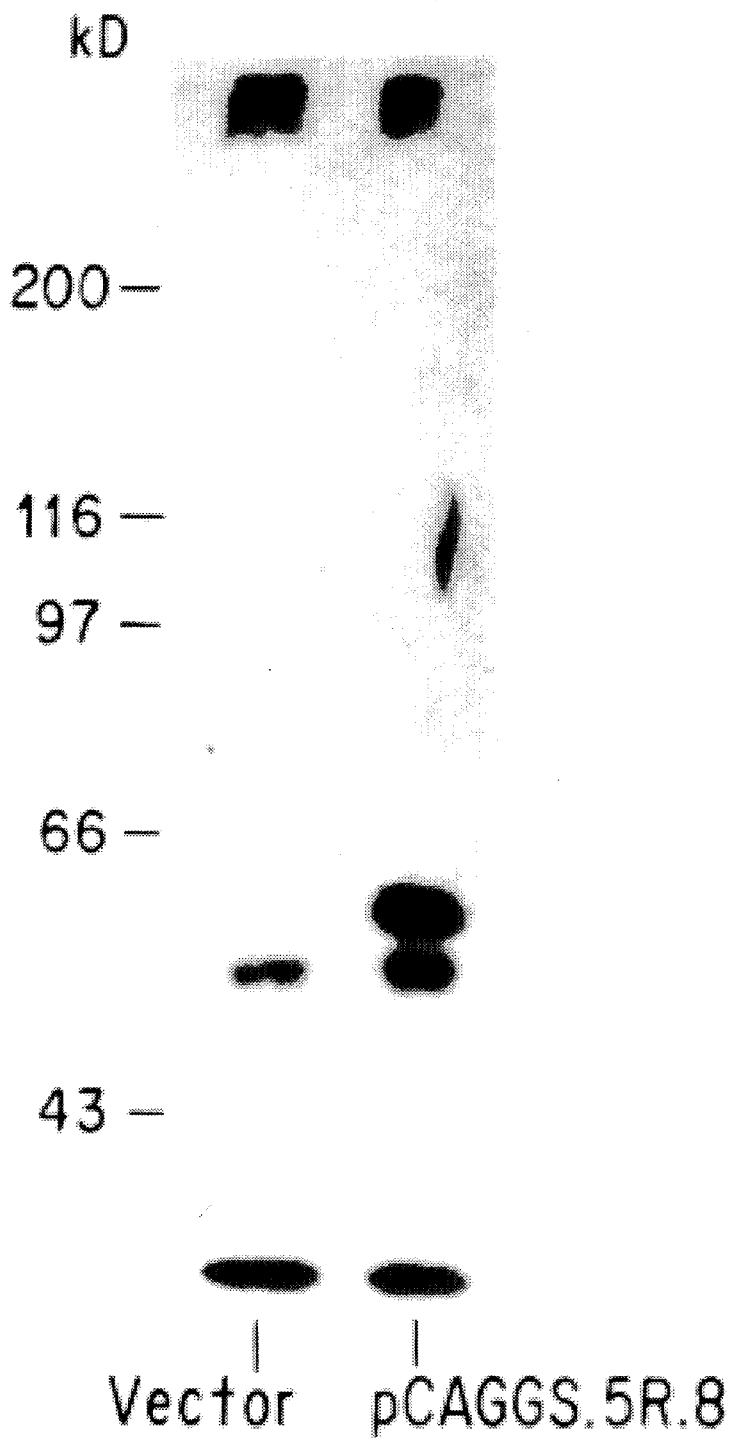
FIG. 5 shows the results of immunoprecipitation of the translated product of mouse IL-5RcDNA that codes for membrane type IL-5R.

The surfaces of the pCAGGS.5R.8 transfected COS7 ($5\times10^6$) cells were labeled with $^{125}$I using Iodobeads (Pierce Chemical, Rockford, Ill.). The cell was disrupted and H7 antibody was added to the cell lysate. Protein G-Sepharose (Pharmacia, Piscataway, N.J.) was added to the mixture and the mixture was incubated at 4° C. for 12 hours. The proteins adsorbed on the Sepharose was loaded on the SDS-PAGE. After electrophoresis under a reducing condition, the gel was analyzed with Bio-Analyzer 100. The band (MW: about 60 KD) was found only in the lane where the sample was prepared from the cell transfected with pCAGGS.5R.8(FIG. 5).

Purification and Amino acid Sequence Analysis of Secretory IL-5R (Murine)

The IL-5R cDNA fragment obtained by XhoI digestion of pIL-5R.2 was inserted into pCAGGS vector by the similar method as in the case of pIL-5R.8 and the construct was designated as pCAGGS.5R.2. E. coli was transformed with the pCAGGS.5R.2 and the transformant was designated as E. coli 5R.2. E. coli 5R.2 was deposited with Fermentation Research Institute, Agency of Industrial Science and Technology and was assigned the accession number FERM BP 3084.

COS7 cells were transfected with pCAGGS.5R.2 DNA according to the DEAE dextran method and was cultured in serum free medium (Iscove's DMEM) for two days. The culture supernatant was concentrated and the concentrate was electrophoresed on SDS-PAGE. A band (MW: approximately 50,000) was found in the lane on which the culture supernatant of pCAGGS.5R.2 transfected COS7 was loaded, while no band was found in the lane on which the culture supernatant of the pCAGGS vector alone was loaded. The culture supernatant of the pCAGGS.5R.2 transfected COS7 was loaded onto a column filled with H7 anibodies bound glycosylhard-gel (Seikagaku Kogyo, Tokyo). The column was washed with 2 mM HEPES solution containing 0.1% CHAPS and then H7 bound fractions were eluted out with 350 mM acetic acid. The fractions were lyophilized and then solubilized in a sample buffer for SDS-PAGE. The mixture was electrophoresed according to the method described by Laemmli in Nature 227: 680, 1970. The protein on the gel was transferred to a polyvinylidene difluoride membrane (Millipore, Bedford, Mass.) according to the electroblotting method. The band corresponding to a molecular weight of about 50,000 was cut out of the membrane and analyzed with a gas phase sequencer 447A (with HPLC system, Applied Biosystem Co.). The amino acid sequence of the N terminus of secretory IL-5R was as follows: Asp-Leu-Leu-Asn-His-Lys-Lys-Phe-Leu-Leu-Leu-Pro-Pro-Val-X-Phe-Thr-Ile-Lys-Ala. This amino acid sequence was found to be the same one (amino acid number 18–37) deduced from the nucleotide sequence of pIL-5R.8, membrane bound IL-5R cDNA clone. The amino acid sequence (amino acid number 1–17) is believed to be a signal peptide. X (amino acid number 15) may be Asn, which is deduced from the nucleotide sequence of cDNA, and to which a N-linked oligosaccharide is believed to bind.

The following Examples are described for human IL-5R.

Preparation of human Poly(A)$^+$RNA

Eosinophils were obtained from 28 liter of peripheral blood of healthy volunteers and 50 ml of peripheral blood of a patient with eosinophilia. After removing erythrocytes, fractions containing eosinophils (1.09 g/ml) were collected from each sample by a density gradient centrifugation using Ficoll. The fraction contained 50% eosinophils and the number of eosinophis was $2.8\times10^9$ [healthy volunteers (helv)] and $2.0\times10^9$ [eosinophilia (eosi)]. 5 μg of poly(A)$^+$ RNA was recovered from each cell source as described above.

Construction of Human IL-5R cDNA Library

5 μg of each poly(A)$^+$ RNA thus obtained was used to synthesize cDNA (helv-cDNA, eosi-cDNA) as described above. The helv-cDNA was ligated to a BstXI linker and a fragment of helv-cDNA-linker complex having a size of 1,000 bp or more was selected. The fragment was then inserted into a BstXI digested pAGS-3 vector. E. coli MC1061 was transformed with the recombinant plasmid and about one million transformants were obtained (helv-cDNA library). The eosi-cDNA was ligated to a EcoRI linker and fragments of eosi-cDNA-linker complex having a size of 1,000 bp or more were selected. The fragments were inserted into a EcoRI digested λgt10 vector. E. coli C600Hfl was infected with the recombinant phage and 1.6 million independent plaques were obtained (eosi-cDNA library).

Screening of helv- and eosi-cDNA libraries according to the colony-hybridization method The helv-cDNA library was screened according to the colony hybridization method. One million colonies of the helv-cDNA library were grown on a solid medium and the colonies were transferred to 100 sheets of nitrocellulose membranes (8 cm in diameter). After DNA fixation, the membrane was placed in a bag containing 10× Denhardt's solution, 6× SSC (0.9M NaCl, 0.09M sodium citrate), 100 µg/ml of heat-denatured salmon sperm DNA. The $^{32}$P-labeled, 1.2 kb HindIII-PstI fragment of pIL-5R.8 was added to the bag and hybridization was carried out at 65° C. for 24 hours under less stringent conditions. The membrane was washed at 45° C. in a solution containing 1× X SSC and 0.1% SDS. After washing, a X-ray film was overlayed on the membrane for autoradiography as described above. A positive clone was obtained and was designated as ph5R.1. However, the cDNA fragment of ph5R.1 was found to contain only 1.0 kb, which was not an right size for IL-5R. Subsequently, the eosi-cDNA library was screened using the XhoI digested, 1.0 kb fragment of ph5R.1 as a probe according to the protocol of Colony/Plaque Screen. Approximately one million clones of the eosi-cDNA library was grown on a solid medium and the plaques were transferred to nylon membranes (13 cm in diameter, Colony/Plaque Screen, Dupont-NEN, Boston, Mass.). Hybridization was carried out at 65° C. for 24 hours in a solution containing 1% SDS, 1M NaCl, 10% Dextran sulfate, 100 µg/ml of heat-denatured salmon sperm DNA. After hybridization, the membrane was washed at 65° C. for an hour in a solution containing 2× X SSC and 1% SDS. Two positive clones containing about 2 kb cDNA fragment were obtained and designated as HSIL5R and HSIL5R2.

E. coli was transformed with HSIL5R or HSIL5R2 and the transformants were designated as E. coli HSIL5R or E. coli HSIL5R2, respectively.

The transformants were deposited with Fermentation Research Institute, Agency of Industrial Science and Technology and were assigned the accession number as follows:

|  | Accession No. |
| --- | --- |
| E. coli HSIL5R | FERM BP-3542 |
| E. coli HSIL5R2 | FERM BP-3543 |

DNA Sequence Analysis of HILS5R and HSIL5R2

HILS5R and HSIL5R2 were digested with EcoRI, and the EcoRI digested IL-5R fragment was inserted into the EcoRI site of Bluescript KS (−) vector (Stratagene, La Jolla, Calif.). The nucleotide sequence was determined according to the Sanger's method. The sequence was determined in both 5' and 3' direction. Initial primers were synthesized according to the sequence of the 5' upstream of the IL-5R cDNA fragment (T3 primer) and of the 3' downstream of the IL-5R cDNA fragment (T7 primer). After the 5' and 3' end sequences were determined, subsequent primers were synthesized according the sequence analyzed by the DNA sequencing. The nucleotide sequence thus determined was found to be complementary.

SEQ ID No. 17 shows the nucleotide and the corresponding amino acid sequence of HSIL5R. The first, 20 amino acids are hypothetically a signal peptide and amino acids 345 to 365 are believed to be a transmembrane region according to hydropathy plot. These assumption are based on the same model as those of mouse. Amino acids 35–37, 131–133, 137–139, 142–144, 216–218, and 244–246 seem to be the sites of N-linked oligosaccharide addition. The estimated molecular weight (45,556) of IL-5R from cDNA clone differs from the real molecular weight (about 60,000) of IL-5R produced by the transformed COS7 cell. The differenece of the weight may be due to the N-linked oligosaccharide. The nucleotide sequence downstream of nucleotide position 1245 distinguishes HSIL5R (SEQ ID No. 17) from HSIL5R2(SEQ ID No. 18).

SEQ ID No. 18 shows the nucleotide and the corresponding amino acid sequence of HSIL5R2. The amino acid sequence of HSIL5R2 terminates at Ile (amino acid number 396), while HSIL5R contains additional 24 amino acids following Ser at amino acid No. 396. The amino acid sequences of HSIL5R and HSIL5R2 are identical from Met (amino acid number 1 ) to Gly (amino acid number 395) except for an amino acid at position 129 where the amino acid is Val on the sequence of HSIL5 and Ile on the sequence of HSIL5R2.

Expression of Human IL-5R on COS7 and Cross-linking experiment

The Bluescript kS (−) recombinant was digested with EcoRI. The restriction fragments containing IL-5R of HSIL5R and HSIL5R2 were inserted into pCAGGS. The resulting constructs were designated as pCAGGS.HSIL-5R and pCAGGS.HSIL5R2. COS7 cells were transfected with these recombinant DNAs and the transformed cells were tested for their chemical characteristics using $^{35}$S-labeled murine IL-5 or $^{125}$I-labeled human IL-5 (2×10$^6$ cpm/µg) according to the cross-linking method.

Figure 7:
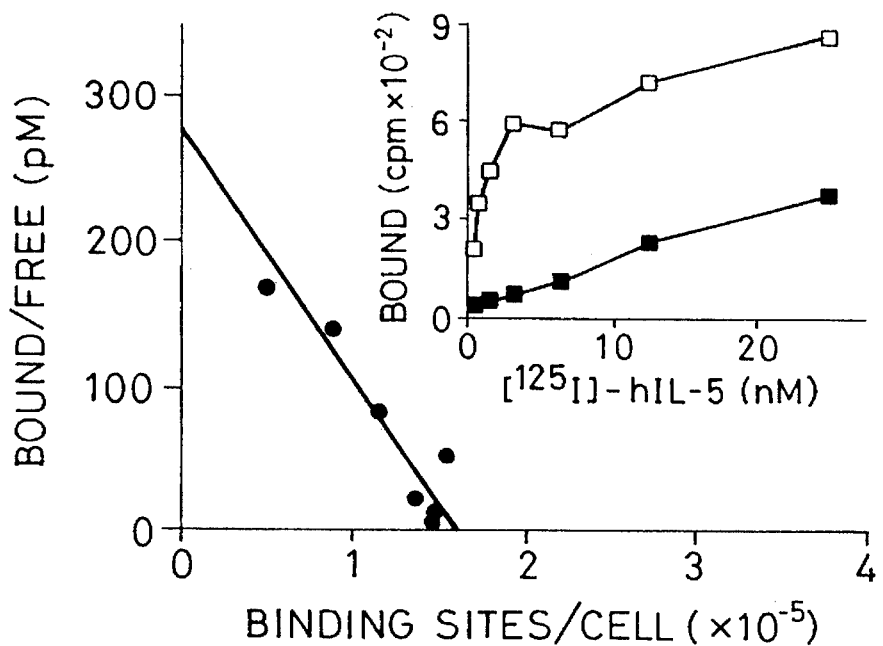
FIGS. 7A–7D shows Scatchard plot analyses of a binding assay of $^{35}$S-labeled murine IL-5 or $^{125}$I labeled human IL-5 to the pCAGGS.HSIL5R or pCAGGS.HSIL5R2 transfected COS 7 cell. The symbol □ represents a total binding and the symbol ■ represents a nonspecific binding in the presence of a 100-fold excess of non-radiolabeled IL-5. COS 7 cells were transfected with pCAGGS.HSIL5R and the transformant was tested for binding using $^{125}$I-labeled human IL-5 (FIG. 7A, inset of FIG. 7A). COS 7 cells were transfected with pCAGGS.HSIL5R2 and the transformant was tested for binding using $^{125}$I-labeled human IL-5 (FIG. 7B, inset of FIG. 7B). COS 7 cells were transfected with pCAGGS.HSIL5R and the transformant was tested for binding using $^{35}$S-labeled mouse IL-5 (FIG. 7C, inset of FIG. 7C). COS 7 cells were transfected with pCAGGS.HSIL5R2 and the transformant was tested for binding using $^{35}$S-labeled mouse IL-5 (FIG. 7D, inset of FIG. 7D).
Figure 7:
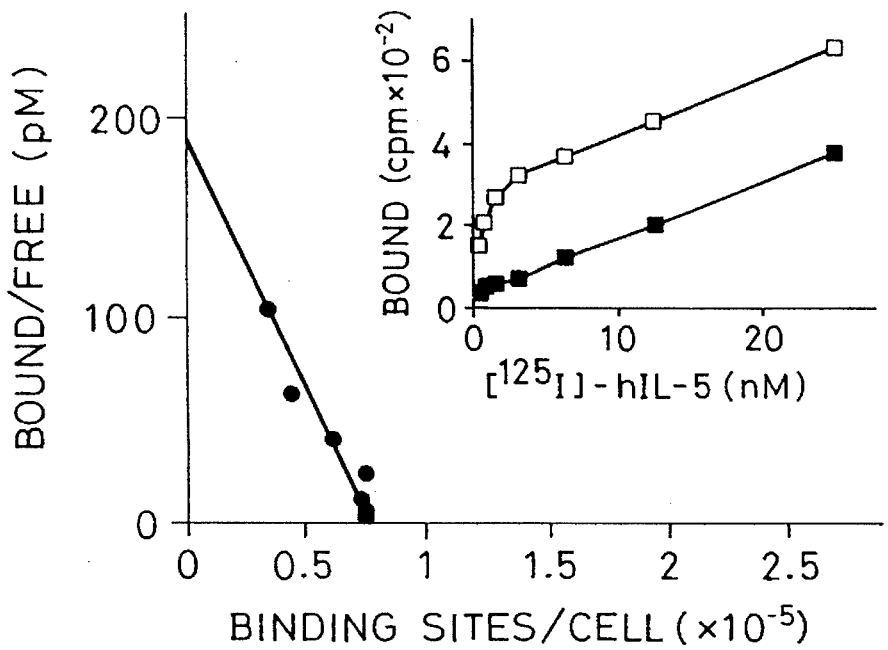
Figure 7:
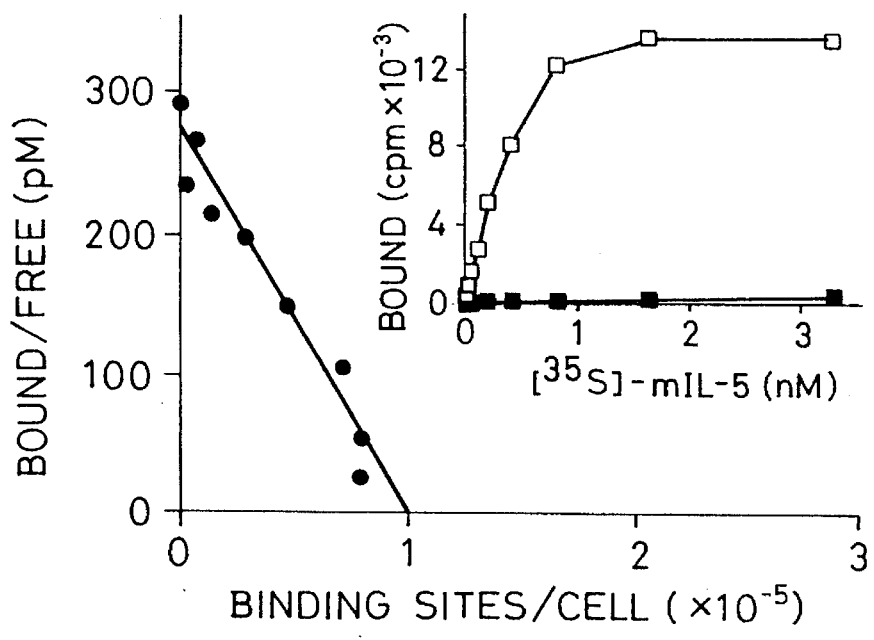
Figure 7:
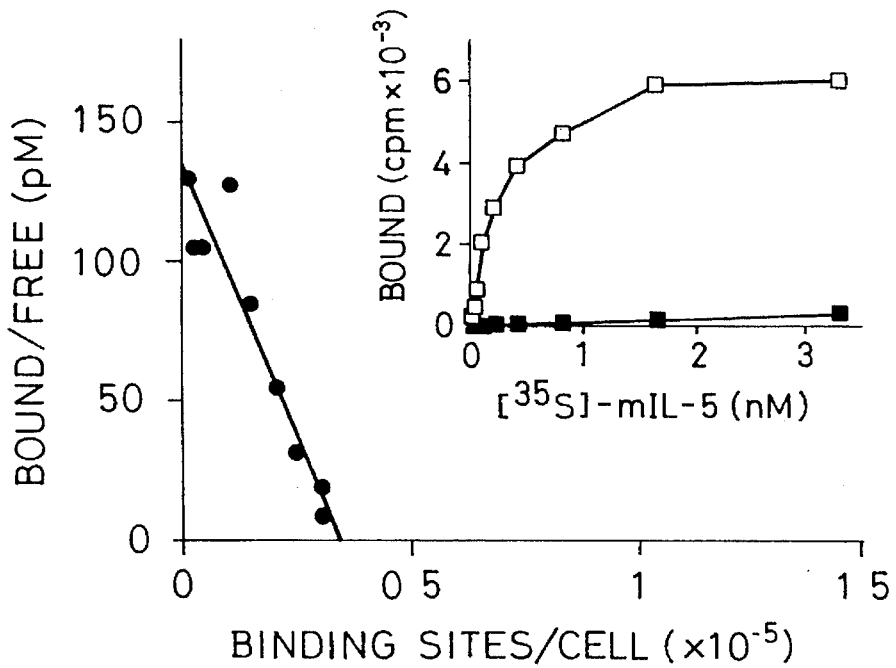

Binding of $^{125}$I-labeled human IL-5 to IL-5R expressed on the COS7 cell (pCAGGS.HSIL5R transformant) was shown in the inset of FIG. 7A, and the results analyzed by Scatchard plot was shown in FIG. 7A. Binding of $^{125}$I-labeled human IL-5 to IL-5R expressed on COS7 cell (pCAGGS.HSIL5R2 transformant) was shown in the inset of FIG. 7B, and the results analyzed by Scatchard plot was shown in FIG. 7B. Binding of $^{35}$S-labeled murine IL-5 to IL-5R expressed on the COS7 cells (pCAGGS.HSIL5R transformant) was shown in the inset of FIG. 7C, and the results analyzed by Scatchard plot was shown in FIG. 7C. Binding of $^{35}$S-labeled murine IL-5 to IL-5R expressed on COS7 cell (pCAGGS.HSIL5R2 transformant) was shown in the inset of FIG. 7D, and the results analyzed by Scatchard plot were shown in FIG. 7D.

A high affinity IL-5R with the dissociation constant (KD) of less than 100 pM was not detectable by $^{125}$I-labeled human IL-5 because of poor specific radioactivity. To calculate the dissociation constant of a high affinity IL-5R, we used $^{35}$S-labeled mouse IL-5 which has high specific radioactivity and is not denatured. The dissociation constant of the pCAGGS.HSIL5R transfected COS7 cells were about 590 pM when radiolabeled human IL-5 was used, while the dissociation constant of the same pCAGGS.HSIL5R transfected COS7 cells were about 250 pM when radiolabeled mouse IL-5 was used. The dissociation constant of the pCAGGS.HSIL5R2 transfected COS7 cells were about 410 pM with radiolabeled human IL-5, while the dissociation constant of the same pCAGGS.HSIL5R2 transfected COS7 cells were about 355 pM when radiolabeled mouse IL-5 was used. These results are comparable to the dissociation constant (170–330 pM) of eosinophils from healthy adult peripheral blood that we reported previously. The data of the previous report were calculated by Scatchard analysis of binding assays using $^{35}$S-labeled mouse IL-5.

The dissociation constant thus determined was higher than that of mouse low affinity IL-5R and fell into the average value of normal human eosinophils. Taken altogether, the isolated IL-5R cDNA fragment was expressed on the surface of the COS7 cells and the IL-5R expressed on the cell surface are responsible for the binding of human IL-5.

Figure 8:
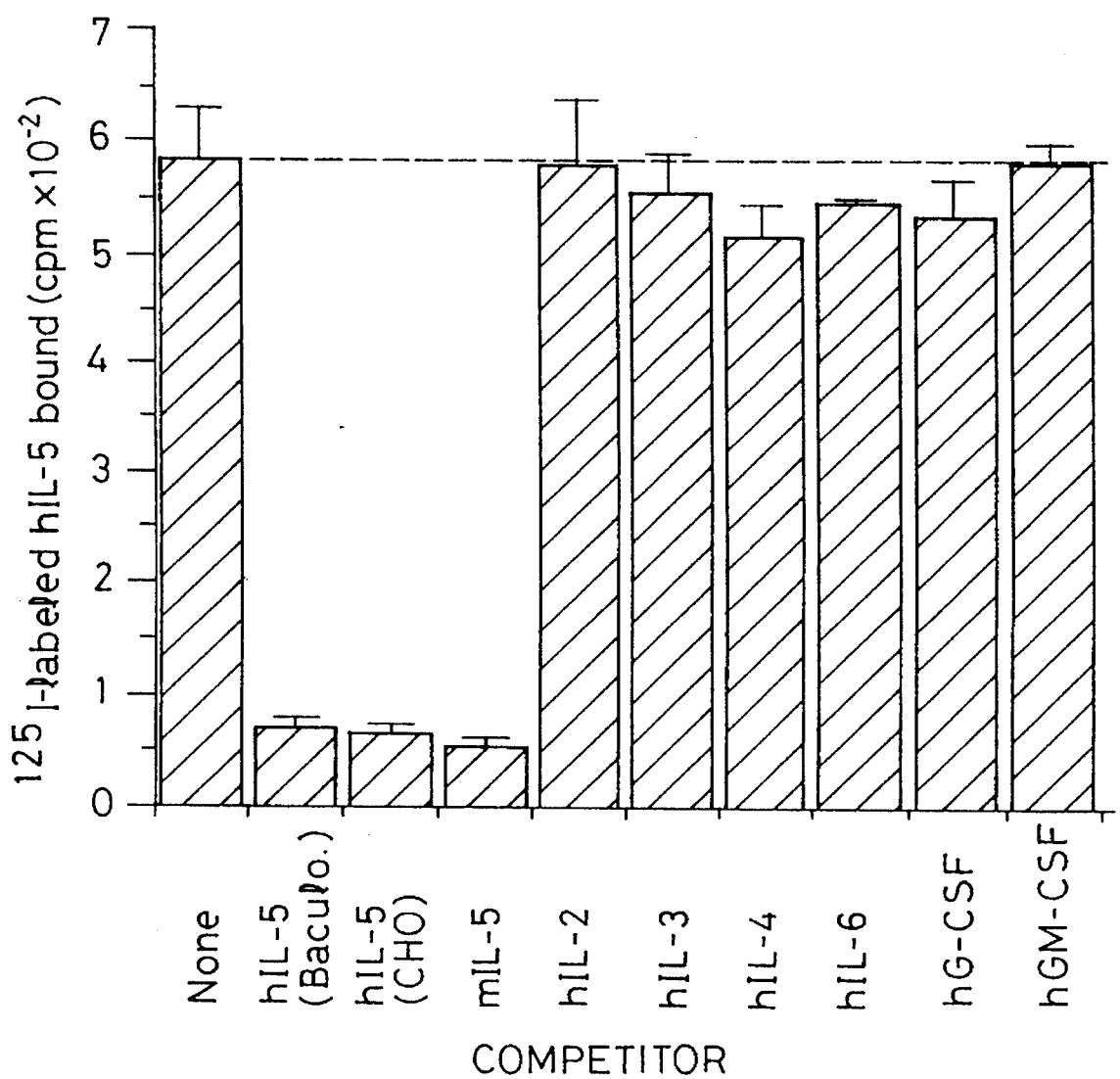
FIG. 8 is a bar graph showing the binding specificity of $^{125}$I labeled human IL-5 to IL-5R. 100 μl of the COS 7 transformants (4×10$^5$ cells) carrying pCAGGS.HSIL5R and 500 pM $^{125}$I-labeled human IL-5 were incubated in the presence of a 1,000-fold excess of cytokines.

FIG. 8 shows inhibitory effects of cytokines on the binding of IL-5 to IL-5R. IL-5R expressed on the COS7 transformants specifically binds to human and mouse IL-5 but not to human IL-2, human IL-3, human IL-4, human IL-6, human GM-CSF or human G-CSF.

Cross-linking of Radiolabeled IL-5 to the COS7 Transformants

The COS7 transformant ($1\times10^5$ cells) carrying pCAGGS.HSIL5R or pCAGGS.HSIL5R2 and either 5.5 nM $^{35}$S-labeled mouse IL-5 or 1 nM $^{125}$I-labeled human IL-5 were mixed in the presence or absence of 250-fold excess of non-labeled IL-5. After one hour incubation at 4° C., 1 mM bis(sulfosuccinimidyl) suberate (Pierce Chemical Co., Rockford, Ill.) was added to the mixture. The mixture was further incubated at 4° C. for 30 minutes. After the incubation, binding was analyzed as described above.

Figure 9:
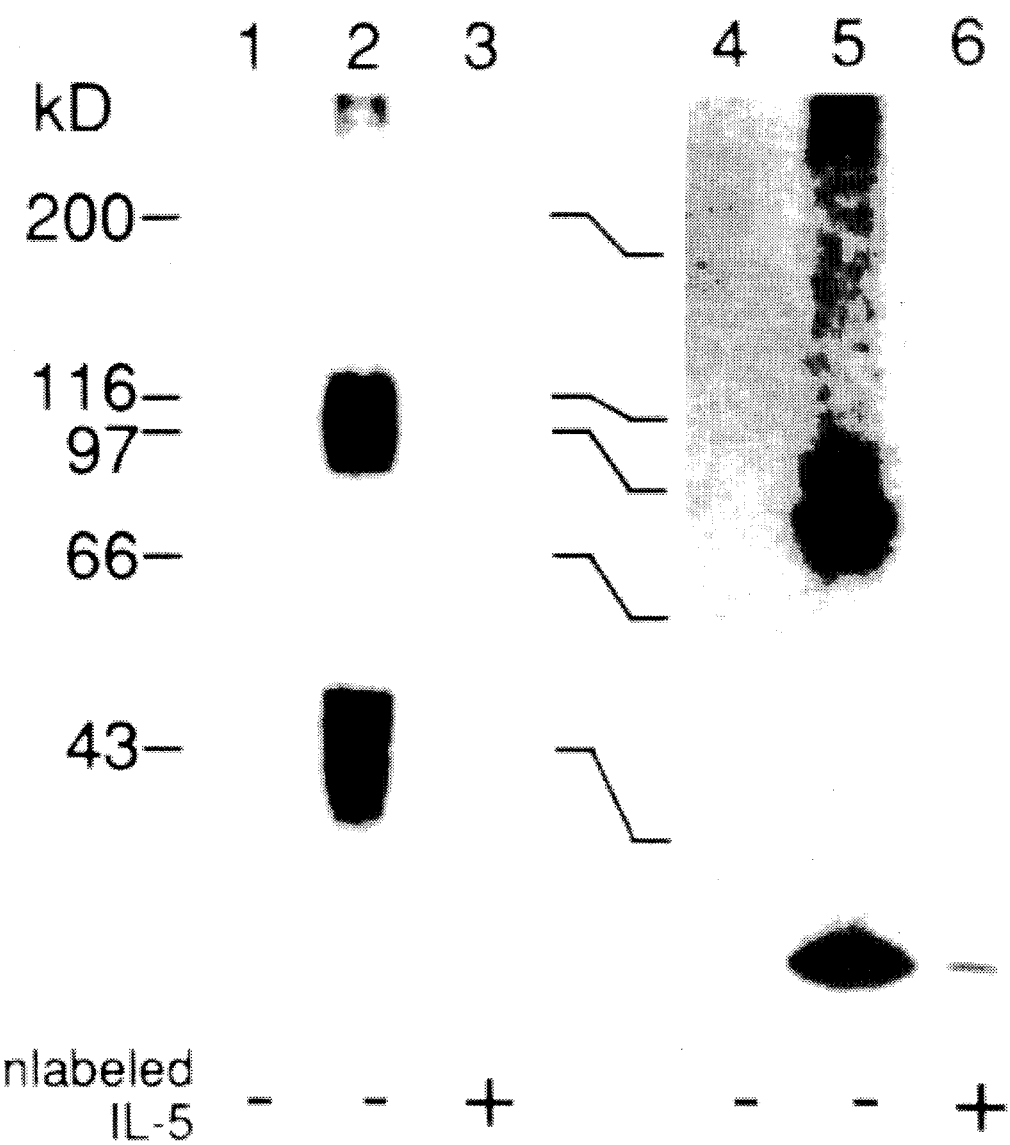
FIG. 9 shows a band pattern of chemical cross-linking of IL-5 analysed by SDS-PAGE. COS cells were transfected with a pCAGGS vector and the transformant was incubated with $^{35}$S-labeled murine IL-5 (lane 1) or $^{125}$I-labeled human IL-5 (lane 4). Then a cross-linking agent, bis(sulfosuccinimidyl) suberate was added to the mixture. After incubation, the mixture was electrophoresed under non-reduced condition. Similarly, COS7 cells were transfected with pCAGGS. HSIL5R and the transformants were incubated with $^{35}$S-labeled murine IL-5 in the presence (lane 3) or absence (lane 2) of an excess amount of non-labeled murine IL-5 or with $^{125}$I-labeled human IL-5 in the presence (lane 6) or absence(lane 5) of an excess amount of non-labeled human IL-5. Then, a cross-linking agent, bis(sulfosuccinimidyl) suberate was added to the mixture. After incubation, the mixture was electrophoresed under non-reducing condition.

In FIG. 9, COS7 cells transfected with a pCAGGS vector alone or pCAGGSHSIL5R were incubated with $^{35}$S-labeled murine IL-5 (A; lane 1, 2, 3) or $^{125}$I-labeled human IL-5(B; lane 4, 5, 6). COS7 cells transfected with a pCAGGS.HSIL5R were incubated with $^{35}$S-labeled murine IL-5 in the presence (lane 3) or absence (lane 2) of 250-fold excess of non-labeled IL-5, or were incubated with $^{125}$I-labeled human IL-5 in the presence (lane 6) or absence (lane 5) of 250-fold excess amount of non-labeled IL-5.

There were two bands corresponding to about 105 kD (lane 2) and 86 kD (lane 5). Since murine IL-5 is 45 kD and human IL-5 is 31 kD, the molecular weight of human IL-5R could be estimated to be 55,000–60,000. This molecular weight of human IL-5R is almost the same as that of IL-5R expressed on eosinophils as we reported previously (Cellular Immunology, 133; 484–469). In the presence of a 250-fold excess of non-labeled IL-5, no band was found (lanes 3, 6 in FIG. 9).

Same experiment was carried out using pCAGGS.HSIL5R2 and the results were very similar to that described above.

What is claimed is:

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 1245 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

```
ATGGTGCCTG TGTTACTAAT TCTTGTGGGA GCTTTGGCAA CACTGCAAGC TGACTTACTT    60
AATCACAAAA AGTTTTTACT TCTACCACCT GTCAATTTTA CCATTAAAGC CACTGGATTA   120
GCTCAAGTTC TTTTACACTG GGACCCAAAT CCTGACCAAG AGCAAAGGCA TGTTGATCTA   180
GAGTATCACG TGAAAATAAA TGCCCCACAA GAAGACGAAT ATGATACCAG AAAGACTGAA   240
AGCAAATGTG TGACCCCCCT TCATGAAGGC TTTGCAGCTA GCGTGAGGAC CATTCTGAAG   300
AGCAGCCATA CAACTCTGGC CAGCAGTTGG GTTTCTGCTG AACTCAAAGC TCCACCAGGA   360
TCTCCTGGAA CCTCGGTTAC GAATTTAACT TGTACCACAC ACACTGTTGT AAGTAGCCAC   420
ACCCACTTAA GGCCATACCA AGTGTCCCTT CGTTGCACCT GGCTTGTTGG GAAGGATGCC   480
CCTGAGGACA CACAGTATTT CCTATACTAC AGGTTTGGTG TTTTGACTGA AAAATGCCAA   540
GAATACAGCA GAGATGCACT GAACAGAAAT ACTGCATGCT GGTTTCCCAG GACATTTATC   600
AACAGCAAAG GGTTTGAACA GCTTGCTGTG CACATTAATG GCTCAAGCAA GCGTGCTGCA   660
ATCAAGCCCT TTGATCAGCT GTTCAGTCCA CTTGCCATTG ACCAAGTGAA TCCTCCAAGG   720
AATGTCACAG TGGAAATTGA AAGCAATTCT CTCTATATAC AGTGGGAGAA ACCACTTTCT   780
GCCTTTCCAG ATCATTGCTT TAACTATGAG CTGAAAATTT ACAACACAAA AAATGGTCAC   840
ATTCAGAAGG AAAAACTGAT CGCCAATAAG TTCATCTCAA AAATTGATGA TGTTTCTACA   900
TATTCCATTC AAGTGAGAGC AGCTGTGAGC TCACCTTGCA GAATGCCAGG AAGGTGGGGC   960
```

| | | | | | |
|---|---|---|---|---|---|
|GAGTGGAGTC|AACCTATTTA|TGTGGGAAAG|GAAAGGAAGT|CCTTGGTAGA|ATGGCATCTC|1020|
|ATTGTGCTCC|CAACAGCTGC|CTGCTTCGTC|TTGTTAATCT|TCTCACTCAT|CTGCAGAGTG|1080|
|TGTCATTTAT|GGACCAGGTT|GTTTCCACCG|GTTCCGGCCC|CAAAGAGTAA|CATCAAAGAT|1140|
|CTCCCTGTGG|TTACTGAATA|TGAGAAACCT|TCGAATGAAA|CCAAAATTGA|AGTTGTACAT|1200|
|TGTGTGGAAG|AGGTTGGATT|TGAAGTCATG|GGAAATTCCA|CGTTT| |1245|

(2) INFORMATION FOR SEQ ID NO:2:

(i) SEQUENCE CHARACTERISTICS:
        (A) LENGTH: 1808 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

| | | | | | |
|---|---|---|---|---|---|
|GAAATAATTG|GTAAACACAG|AAAATGTTTC|AATAGAAAAA|AGAGGAAACA|GAACACTGTG|60|
|TAGCCCTGTT|ATCAGCAGAG|ACAGAGCTAA|CGCTGGGGAT|ACCAAACTAG|AAGAAGCTCA|120|
|CTGGACAGGT|CCCGGTATGC|AGTTCTATTT|TTGTTGATGG|CTCTGTATCT|AATGTGTTCA|180|
|TTTGTACCAA|GGATCTAACC|AGGGTCTTCC|AGAGTCTGAG|CAAGCTTCTC|CCACTGAGCT|240|
|ACATCACAGC|CCCCTGTTTA|TTGGAAGAAG|AAATACTTAC|ACCTTTCCAG|TATTCGGCTA|300|
|CCATGGTGCC|TGTGTTACTA|ATTCTTGTGG|GAGCTTTGGC|AACACTGCAA|GCTGACTTAC|360|
|TTAATCACAA|AAAGTTTTTA|CTTCTACCAC|CTGTCAATTT|TACCATTAAA|GCCACTGGAT|420|
|TAGCTCAAGT|TCTTTTACAC|TGGGACCCAA|ATCCTGACCA|AGAGCAAAGG|CATGTTGATC|480|
|TAGAGTATCA|CGTGAAAATA|AATGCCCCAC|AAGAAGACGA|ATATGATACC|AGAAAGACTG|540|
|AAAGCAAATG|TGTGACCCCC|CTTCATGAAG|CTTTGCAGC|TAGCGTGAGG|ACCATTCTGA|600|
|AGAGCAGCCA|TACAACTCTG|GCCAGCAGTT|GGGTTTCTGC|TGAACTCAAA|GCTCCACCAG|660|
|GATCTCCTGG|AACCTCGGTT|ACGAATTTAA|CTTGTACCAC|ACACACTGTT|GTAAGTAGCC|720|
|ACACCCACTT|AAGGCCATAC|CAAGTGTCCC|TTCGTTGCAC|CTGGCTTGTT|GGGAAGGATG|780|
|CCCCTGAGGA|CACACAGTAT|TTCCTATACT|ACAGGTTTGG|TGTTTTGACT|GAAAAATGCC|840|
|AAGAATACAG|CAGAGATGCA|CTGAACAGAA|ATACTGCATG|CTGGTTTCCC|AGGACATTTA|900|
|TCAACAGCAA|AGGGTTTGAA|CAGCTTGCTG|TGCACATTAA|TGGCTCAAGC|AAGCGTGCTG|960|
|CAATCAAGCC|CTTTGATCAG|CTGTTCAGTC|CACTTGCCAT|TGACCAAGTG|AATCCTCCAA|1020|
|GGAATGTCAC|AGTGGAAATT|GAAAGCAATT|CTCTCTATAT|ACAGTGGGAG|AAACCACTTT|1080|
|CTGCCTTTCC|AGATCATTGC|TTTAACTATG|AGCTGAAAAT|TTACAACACA|AAAAATGGTC|1140|
|ACATTCAGAA|GGAAAAACTG|ATCGCCAATA|AGTTCATCTC|AAAAATTGAT|GATGTTTCTA|1200|
|CATATTCCAT|TCAAGTGAGA|GCAGCTGTGA|GCTCACCTTG|CAGAATGCCA|GGAAGGTGGG|1260|
|GCGAGTGGAG|TCAACCTATT|TATGTGGGAA|AGGAAAGGAA|GTCCTTGGTA|GAATGGCATC|1320|
|TCATTGTGCT|CCCAACAGCT|GCCTGCTTCG|TCTTGTTAAT|CTTCTCACTC|ATCTGCAGAG|1380|
|TGTGTCATTT|ATGGACCAGG|TTGTTTCCAC|CGGTTCCGGC|CCAAAGAGT|AACATCAAAG|1440|
|ATCTCCCTGT|GGTTACTGAA|TATGAGAAAC|CTTCGAATGA|AACCAAAATT|GAAGTTGTAC|1500|
|ATTGTGTGGA|AGAGGTTGGA|TTTGAAGTCA|TGGGAAATTC|CACGTTTTGA|TGGCATTTTG|1560|
|CCATTCTGAA|ATGAACTCAT|ACAGGACTCC|GTGATAAGAG|CAAGGACTGC|TATTTCTTGG|1620|
|CAAGGAGGTA|TTTCAAATGA|ACACTCAGAG|CCAGGCGGTG|GTAGAGCTCG|CCTTTAATAC|1680|

| | | | | | |
|---|---|---|---|---|---|
| CAGCACCTGG | GATGCACAGA | CGGGAGGATT | TCTGAGTTCG | AGGCCAGCTT | GGTCTATAAA | 1740 |
| GTGAGTTCCA | GGACAGCCAG | AGCTACACAG | AGAAACCCTG | TCTCGAAAAA | ACAAACAAAC | 1800 |
| AAACAAAC | | | | | | 1808 |

(2) INFORMATION FOR SEQ ID NO:3:

(i) SEQUENCE CHARACTERISTICS:
        (A) LENGTH: 996 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

| | | | | | |
|---|---|---|---|---|---|
| ATGGTGCCTG | TGTTACTAAT | TCTTGTGGGA | GCTTTGGCAA | CACTGCAAGC | TGACTTACTT | 60 |
| AATCACAAAA | AGTTTTTACT | TCTACCACCT | GTCAATTTTA | CCATTAAAGC | CACTGGATTA | 120 |
| GCTCAAGTTC | TTTTACACTG | GGACCCAAAT | CCTGACCAAG | AGCAAAGGCA | TGTTGATCTA | 180 |
| GAGTATCACG | TGAAAATAAA | TGCCCCACAA | GAAGACGAAT | ATGATACCAG | AAAGACTGAA | 240 |
| AGCAAATGTG | TGACCCCCCT | TCATGAAGGC | TTTGCAGCTA | GCGTGAGGAC | CATTCTGAAG | 300 |
| AGCAGCCATA | CAACTCTGGC | CAGCAGTTGG | GTTTCTGCTG | AACTCAAAGC | TCCACCAGGA | 360 |
| TCTCCTGGAA | CCTCGGTTAC | GAATTTAACT | TGTACCACAC | ACACTGTTGT | AAGTAGCCAC | 420 |
| ACCCACTTAA | GGCCATACCA | AGTGTCCCTT | CGTTGCACCT | GGCTTGTTGG | GAAGGATGCC | 480 |
| CCTGAGGACA | CACAGTATTT | CCTATACTAC | AGGTTTGGTG | TTTTGACTGA | AAAATGCCAA | 540 |
| GAATACAGCA | GAGATGCACT | GAACAGAAAT | ACTGCATGCT | GGTTTCCCAG | ACATTTATC | 600 |
| AACAGCAAAG | GGTTTGAACA | GCTTGCTGTG | CACATTAATG | GCTCAAGCAA | GCGTGCTGCA | 660 |
| ATCAAGCCCT | TTGATCAGCT | GTTCAGTCCA | CTTGCCATTG | ACCAAGTGAA | TCCTCCAAGG | 720 |
| AATGTCACAG | TGGAAATTGA | AAGCAATTCT | CTCTATATAC | AGTGGGAGAA | ACCACTTTCT | 780 |
| GCCTTTCCAG | ATCATTGCTT | TAACTATGAG | CTGAAAATTT | ACAACACAAA | AAATGGTCAC | 840 |
| ATTCAGAAGG | AAAAACTGAT | CGCCAATAAG | TTCATCTCAA | AAATTGATGA | TGTTTCTACA | 900 |
| TATTCCATTC | AAGTGAGAGC | AGCTGTGAGC | TCACCTTGCA | GAATGCCAGG | AAGGTGGGGC | 960 |
| GAGTGGAGTC | AACCTATTTA | TGTGGAAACC | TTCGAA | | | 996 |

(2) INFORMATION FOR SEQ ID NO:4:

(i) SEQUENCE CHARACTERISTICS:
        (A) LENGTH: 1355 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

| | | | | | |
|---|---|---|---|---|---|
| TATTCGGCTA | CCATGGTGCC | TGTGTTACTA | ATTCTTGTGG | GAGCTTTGGC | AACACTGCAA | 60 |
| GCTGACTTAC | TTAATCACAA | AAAGTTTTTA | CTTCTACCAC | CTGTCAATTT | TACCATTAAA | 120 |
| GCCACTGGAT | TAGCTCAAGT | TCTTTTACAC | TGGGACCCAA | ATCCTGACCA | AGAGCAAAGG | 180 |
| CATGTTGATC | TAGAGTATCA | CGTGAAAATA | AATGCCCCAC | AAGAAGACGA | ATATGATACC | 240 |
| AGAAAGACTG | AAAGCAAATG | TGTGACCCCC | CTTCATGAAG | GCTTTGCAGC | TAGCGTGAGG | 300 |
| ACCATTCTGA | AGAGCAGCCA | TACAACTCTG | GCCAGCAGTT | GGGTTTCTGC | TGAACTCAAA | 360 |
| GCTCCACCAG | GATCTCCTGG | AACCTCGGTT | ACGAATTTAA | CTTGTACCAC | ACACACTGTT | 420 |

-continued

```
GTAAGTAGCC ACACCCACTT AAGGCCATAC CAAGTGTCCC TTCGTTGCAC CTGGCTTGTT        480
GGGAAGGATG CCCCTGAGGA CACACAGTAT TTCCTATACT ACAGGTTTGG TGTTTTGACT        540
GAAAAATGCC AAGAATACAG CAGAGATGCA CTGAACAGAA ATACTGCATG CTGGTTTCCC        600
AGGACATTTA TCAACAGCAA AGGGTTTGAA CAGCTTGCTG TGCACATTAA TGGCTCAAGC        660
AAGCGTGCTG CAATCAAGCC CTTTGATCAG CTGTTCAGTC CACTTGCCAT TGACCAAGTG        720
AATCCTCCAA GGAATGTCAC AGTGGAAATT GAAAGCAATT CTCTCTATAT ACAGTGGGAG        780
AAACCACTTT CTGCCTTTCC AGATCATTGC TTTAACTATG AGCTGAAAAT TTACAACACA        840
AAAAATGGTC ACATTCAGAA GGAAAAACTG ATCGCCAATA AGTTCATCTC AAAAATTGAT        900
GATGTTTCTA CATATTCCAT TCAAGTGAGA GCAGCTGTGA GCTCACCTTG CAGAATGCCA        960
GGAAGGTGGG GCGAGTGGAG TCAACCTATT TATGTGGAAA CCTTCGAATG AAACCAAAAT       1020
TGAAGTTGTA CATTGTGTGG AAGAGGTTGG ATTTGAAGTC ATGGGAAATT CCACGTTTTG       1080
ATGGCATTTT GCCATTCTGA AATGAACTCA TACAGGACTC CGTGATAAGA GCAAGGACTG       1140
CTATTTCTTG GCAAGGAGGT ATTTCAAATG AACACTCAGA GCCAGGCGGT GGTAGAGCTC       1200
GCCTTTAATA CCAGCACCTG GGATGCACAG ACGGGAGGAT TTCTGAGTTC GAGGCCAGCT       1260
TGGTCTATAA AGTGAGTTCC AGGACAGCCA GAGCTACACA GAGAAACCCT GTCTCGAAAA       1320
AACAAACAAA CAAACAAACA AACAAAAATG AACAC                                  1355
```

(2) INFORMATION FOR SEQ ID NO:5:

(i) SEQUENCE CHARACTERISTICS:
        (A) LENGTH: 415 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:5:

```
Met Val Pro Val Leu Leu Ile Leu Val Gly Ala Leu Ala Thr Leu Gln
 1               5                  10                  15

Ala Asp Leu Leu Asn His Lys Lys Phe Leu Leu Leu Pro Pro Val Asn
            20                  25                  30

Phe Thr Ile Lys Ala Thr Gly Leu Ala Gln Val Leu Leu His Trp Asp
        35                  40                  45

Pro Asn Pro Asp Gln Glu Gln Arg His Val Asp Leu Glu Tyr His Val
    50                  55                  60

Lys Ile Asn Ala Pro Gln Glu Asp Glu Tyr Asp Thr Arg Lys Thr Glu
65                  70                  75                  80

Ser Lys Cys Val Thr Pro Leu His Glu Gly Phe Ala Ala Ser Val Arg
            85                  90                  95

Thr Ile Leu Lys Ser Ser His Thr Thr Leu Ala Ser Ser Trp Val Ser
            100                 105                 110

Ala Glu Leu Lys Ala Pro Pro Gly Ser Pro Gly Thr Ser Val Thr Asn
            115                 120                 125

Leu Thr Cys Thr Thr His Thr Val Val Ser Ser His Thr His Leu Arg
    130                 135                 140

Pro Tyr Gln Val Ser Leu Arg Cys Thr Trp Leu Val Gly Lys Asp Ala
145                 150                 155                 160

Pro Glu Asp Thr Gln Tyr Phe Leu Tyr Tyr Arg Phe Gly Val Leu Thr
                165                 170                 175
```

```
Glu  Lys  Cys  Gln  Glu  Tyr  Ser  Arg  Asp  Ala  Leu  Asn  Arg  Asn  Thr  Ala
               180                      185                     190

Cys  Trp  Phe  Pro  Arg  Thr  Phe  Ile  Asn  Ser  Lys  Gly  Phe  Glu  Gln  Leu
          195                      200                     205

Ala  Val  His  Ile  Asn  Gly  Ser  Ser  Lys  Arg  Ala  Ala  Ile  Lys  Pro  Phe
          210                      215                     220

Asp  Gln  Leu  Phe  Ser  Pro  Leu  Ala  Ile  Asp  Gln  Val  Asn  Pro  Pro  Arg
225                      230                     235                          240

Asn  Val  Thr  Val  Glu  Ile  Glu  Ser  Asn  Ser  Leu  Tyr  Ile  Gln  Trp  Glu
               245                      250                     255

Lys  Pro  Leu  Ser  Ala  Phe  Pro  Asp  His  Cys  Phe  Asn  Tyr  Glu  Leu  Lys
               260                      265                     270

Ile  Tyr  Asn  Thr  Lys  Asn  Gly  His  Ile  Gln  Lys  Glu  Lys  Leu  Ile  Ala
          275                      280                     285

Asn  Lys  Phe  Ile  Ser  Lys  Ile  Asp  Asp  Val  Ser  Thr  Tyr  Ser  Ile  Gln
          290                      295                     300

Val  Arg  Ala  Ala  Val  Ser  Pro  Cys  Arg  Met  Pro  Gly  Arg  Trp  Gly
305                      310                     315                          320

Glu  Trp  Ser  Gln  Pro  Ile  Tyr  Val  Gly  Lys  Glu  Arg  Lys  Ser  Leu  Val
                    325                     330                     335

Glu  Trp  His  Leu  Ile  Val  Leu  Pro  Thr  Ala  Ala  Cys  Phe  Val  Leu  Leu
               340                      345                     350

Ile  Phe  Ser  Leu  Ile  Cys  Arg  Val  Cys  His  Leu  Trp  Thr  Arg  Leu  Phe
          355                      360                     365

Pro  Pro  Val  Pro  Ala  Pro  Lys  Ser  Asn  Ile  Lys  Asp  Leu  Pro  Val  Val
     370                      375                     380

Thr  Glu  Tyr  Glu  Lys  Pro  Ser  Asn  Glu  Thr  Lys  Ile  Glu  Val  Val  His
385                      390                     395                          400

Cys  Val  Glu  Glu  Val  Gly  Phe  Glu  Val  Met  Gly  Asn  Ser  Thr  Phe
               405                      410                     415
```

( 2 ) INFORMATION FOR SEQ ID NO:6:

( i ) SEQUENCE CHARACTERISTICS:
        ( A ) LENGTH: 398 amino acids
        ( B ) TYPE: amino acid
        ( C ) STRANDEDNESS: unknown
        ( D ) TOPOLOGY: linear ( i i ) MOLECULE TYPE: peptide ( x i ) SEQUENCE DESCRIPTION: SEQ ID NO:6:

```
Asp  Leu  Leu  Asn  His  Lys  Lys  Phe  Leu  Leu  Pro  Pro  Val  Asn  Phe
1                   5                        10                      15

Thr  Ile  Lys  Ala  Thr  Gly  Leu  Ala  Gln  Val  Leu  Leu  His  Trp  Asp  Pro
               20                       25                      30

Asn  Pro  Asp  Gln  Glu  Gln  Arg  His  Val  Asp  Leu  Glu  Tyr  His  Val  Lys
          35                       40                      45

Ile  Asn  Ala  Pro  Gln  Glu  Asp  Glu  Tyr  Asp  Thr  Arg  Lys  Thr  Glu  Ser
          50                       55                      60

Lys  Cys  Val  Thr  Pro  Leu  His  Glu  Gly  Phe  Ala  Ala  Ser  Val  Arg  Thr
65                       70                       75                          80

Ile  Leu  Lys  Ser  Ser  His  Thr  Thr  Leu  Ala  Ser  Ser  Trp  Val  Ser  Ala
               85                       90                      95

Glu  Leu  Lys  Ala  Pro  Pro  Gly  Ser  Pro  Gly  Thr  Ser  Val  Thr  Asn  Leu
               100                      105                     110
```

| | | | | | | | | | | | | | | |
|---|---|---|---|---|---|---|---|---|---|---|---|---|---|---|
|Thr|Cys|Thr|Thr|His|Thr|Val|Val|Ser|Ser|His|Thr|His|Leu|Arg|Pro|
| |115| | | | |120| | | | |125| | | |
|Tyr|Gln|Val|Ser|Leu|Arg|Cys|Thr|Trp|Leu|Val|Gly|Lys|Asp|Ala|Pro|
| |130| | | | |135| | | | |140| | | |
|Glu|Asp|Thr|Gln|Tyr|Phe|Leu|Tyr|Tyr|Arg|Phe|Gly|Val|Leu|Thr|Glu|
|145| | | | |150| | | | |155| | | | |160|
|Lys|Cys|Gln|Glu|Tyr|Ser|Arg|Asp|Ala|Leu|Asn|Arg|Asn|Thr|Ala|Cys|
| | | | |165| | | | |170| | | | |175| |
|Trp|Phe|Pro|Arg|Thr|Phe|Ile|Asn|Ser|Lys|Gly|Phe|Glu|Gln|Leu|Ala|
| | | |180| | | | |185| | | | |190| | |
|Val|His|Ile|Asn|Gly|Ser|Ser|Lys|Arg|Ala|Ala|Ile|Lys|Pro|Phe|Asp|
| | |195| | | | |200| | | | |205| | | |
|Gln|Leu|Phe|Ser|Pro|Leu|Ala|Ile|Asp|Gln|Val|Asn|Pro|Pro|Arg|Asn|
| |210| | | | |215| | | | |220| | | | |
|Val|Thr|Val|Glu|Ile|Glu|Ser|Asn|Ser|Leu|Tyr|Ile|Gln|Trp|Glu|Lys|
|225| | | | |230| | | | |235| | | | |240|
|Pro|Leu|Ser|Ala|Phe|Pro|Asp|His|Cys|Phe|Asn|Tyr|Glu|Leu|Lys|Ile|
| | | | |245| | | | |250| | | | |255| |
|Tyr|Asn|Thr|Lys|Asn|Gly|His|Ile|Gln|Lys|Glu|Lys|Leu|Ile|Ala|Asn|
| | | |260| | | | |265| | | | |270| | |
|Lys|Phe|Ile|Ser|Lys|Ile|Asp|Asp|Val|Ser|Thr|Tyr|Ser|Ile|Gln|Val|
| | |275| | | | |280| | | | |285| | | |
|Arg|Ala|Ala|Val|Ser|Ser|Pro|Cys|Arg|Met|Pro|Gly|Arg|Trp|Gly|Glu|
| |290| | | | |295| | | | |300| | | | |
|Trp|Ser|Gln|Pro|Ile|Tyr|Val|Gly|Lys|Glu|Arg|Lys|Ser|Leu|Val|Glu|
|305| | | | |310| | | | |315| | | | |320|
|Trp|His|Leu|Ile|Val|Leu|Pro|Thr|Ala|Ala|Cys|Phe|Val|Leu|Leu|Ile|
| | | |325| | | | |330| | | | |335| | |
|Phe|Ser|Leu|Ile|Cys|Arg|Val|Cys|His|Leu|Trp|Thr|Arg|Leu|Phe|Pro|
| | | |340| | | | |345| | | | |350| | |
|Pro|Val|Pro|Ala|Pro|Lys|Ser|Asn|Ile|Lys|Asp|Leu|Pro|Val|Val|Thr|
| | |355| | | | |360| | | | |365| | | |
|Glu|Tyr|Glu|Lys|Pro|Ser|Asn|Glu|Thr|Lys|Ile|Glu|Val|Val|His|Cys|
| |370| | | | |375| | | | |380| | | | |
|Val|Glu|Glu|Val|Gly|Phe|Glu|Val|Met|Gly|Asn|Ser|Thr|Phe| | |
|385| | | | |390| | | | |395| | | | | |

( 2 ) INFORMATION FOR SEQ ID NO:7:

( i ) SEQUENCE CHARACTERISTICS:
        ( A ) LENGTH: 332 amino acids
        ( B ) TYPE: amino acid
        ( C ) STRANDEDNESS: unknown
        ( D ) TOPOLOGY: linear ( i i ) MOLECULE TYPE: peptide ( x i ) SEQUENCE DESCRIPTION: SEQ ID NO:7:

| | | | | | | | | | | | | | | |
|---|---|---|---|---|---|---|---|---|---|---|---|---|---|---|
|Met|Val|Pro|Val|Leu|Leu|Ile|Leu|Val|Gly|Ala|Leu|Ala|Thr|Leu|Gln|
|1| | | |5| | | | |10| | | | |15| |
|Ala|Asp|Leu|Leu|Asn|His|Lys|Lys|Phe|Leu|Leu|Leu|Pro|Pro|Val|Asn|
| | | |20| | | | |25| | | | |30| | |
|Phe|Thr|Ile|Lys|Ala|Thr|Gly|Leu|Ala|Gln|Val|Leu|Leu|His|Trp|Asp|
| | |35| | | | |40| | | | |45| | | |
|Pro|Asn|Pro|Asp|Gln|Glu|Gln|Arg|His|Val|Asp|Leu|Glu|Tyr|His|Val|
| |50| | | | |55| | | | |60| | | | |

```
Lys  Ile  Asn  Ala  Pro  Gln  Glu  Asp  Glu  Tyr  Asp  Thr  Arg  Lys  Thr  Glu
 65                      70                       75                       80

Ser  Lys  Cys  Val  Thr  Pro  Leu  His  Glu  Gly  Phe  Ala  Ala  Ser  Val  Arg
                         85                       90                       95

Thr  Ile  Leu  Lys  Ser  Ser  His  Thr  Thr  Leu  Ala  Ser  Ser  Trp  Val  Ser
               100                      105                     110

Ala  Glu  Leu  Lys  Ala  Pro  Pro  Gly  Ser  Pro  Gly  Thr  Ser  Val  Thr  Asn
          115                           120                     125

Leu  Thr  Cys  Thr  Thr  His  Thr  Val  Val  Ser  Ser  His  Thr  His  Leu  Arg
     130                      135                          140

Pro  Tyr  Gln  Val  Ser  Leu  Arg  Cys  Thr  Trp  Leu  Val  Gly  Lys  Asp  Ala
145                      150                      155                      160

Pro  Glu  Asp  Thr  Gln  Tyr  Phe  Leu  Tyr  Tyr  Arg  Phe  Gly  Val  Leu  Thr
                    165                      170                     175

Glu  Lys  Cys  Gln  Glu  Tyr  Ser  Arg  Asp  Ala  Leu  Asn  Arg  Asn  Thr  Ala
               180                      185                     190

Cys  Trp  Phe  Pro  Arg  Thr  Phe  Ile  Asn  Ser  Lys  Gly  Phe  Glu  Gln  Leu
          195                      200                     205

Ala  Val  His  Ile  Asn  Gly  Ser  Ser  Lys  Arg  Ala  Ala  Ile  Lys  Pro  Phe
     210                      215                     220

Asp  Gln  Leu  Phe  Ser  Pro  Leu  Ala  Ile  Asp  Gln  Val  Asn  Pro  Pro  Arg
225                      230                     235                      240

Asn  Val  Thr  Val  Glu  Ile  Glu  Ser  Asn  Ser  Leu  Tyr  Ile  Gln  Trp  Glu
               245                      250                     255

Lys  Pro  Leu  Ser  Ala  Phe  Pro  Asp  His  Cys  Phe  Asn  Tyr  Glu  Leu  Lys
               260                      265                     270

Ile  Tyr  Asn  Thr  Lys  Asn  Gly  His  Ile  Gln  Lys  Glu  Lys  Leu  Ile  Ala
          275                      280                     285

Asn  Lys  Phe  Ile  Ser  Lys  Ile  Asp  Asp  Val  Ser  Thr  Tyr  Ser  Ile  Gln
     290                      295                     300

Val  Arg  Ala  Ala  Val  Ser  Ser  Pro  Cys  Arg  Met  Pro  Gly  Arg  Trp  Gly
305                           310                     315                 320

Glu  Trp  Ser  Gln  Pro  Ile  Tyr  Val  Glu  Thr  Phe  Glu
               325                      330
```

(2) INFORMATION FOR SEQ ID NO:8:

(i) SEQUENCE CHARACTERISTICS:
        (A) LENGTH: 315 amino acids
        (B) TYPE: amino acid
        (C) STRANDEDNESS: unknown
        (D) TOPOLOGY: linear (ii) MOLECULE TYPE: peptide (xi) SEQUENCE DESCRIPTION: SEQ ID NO:8:

```
Asp  Leu  Leu  Asn  His  Lys  Lys  Phe  Leu  Leu  Pro  Pro  Val  Asn  Phe
 1                  5                       10                      15

Thr  Ile  Lys  Ala  Thr  Gly  Leu  Ala  Gln  Val  Leu  Leu  His  Trp  Asp  Pro
               20                       25                      30

Asn  Pro  Asp  Gln  Glu  Gln  Arg  His  Val  Asp  Leu  Glu  Tyr  His  Val  Lys
          35                           40                      45

Ile  Asn  Ala  Pro  Gln  Glu  Asp  Glu  Tyr  Asp  Thr  Arg  Lys  Thr  Glu  Ser
     50                       55                      60

Lys  Cys  Val  Thr  Pro  Leu  His  Glu  Gly  Phe  Ala  Ala  Ser  Val  Arg  Thr
 65                      70                      75                      80
```

|     |     |     |     |     |     |     |     |     |     |     |     |     |     |     |
| --- | --- | --- | --- | --- | --- | --- | --- | --- | --- | --- | --- | --- | --- | --- |
| Ile | Leu | Lys | Ser | Ser  | His | Thr | Thr | Leu  | Ala | Ser | Ser | Trp | Val | Ser  | Ala |
|     |     |     |     | 85   |     |     |     | 90   |     |     |     |     |     | 95   |     |
| Glu | Leu | Lys | Ala | Pro  | Pro | Gly | Ser | Pro  | Gly | Thr | Ser | Val | Thr | Asn  | Leu |
|     |     |     | 100 |      |     |     |     | 105  |     |     |     |     | 110 |      |     |
| Thr | Cys | Thr | Thr | His  | Thr | Val | Val | Ser  | Ser | His | Thr | His | Leu | Arg  | Pro |
|     |     | 115 |     |      |     |     | 120 |      |     |     |     | 125 |     |      |     |
| Tyr | Gln | Val | Ser | Leu  | Arg | Cys | Thr | Trp  | Leu | Val | Gly | Lys | Asp | Ala  | Pro |
|     | 130 |     |     |      |     | 135 |     |      |     |     | 140 |     |     |      |     |
| Glu | Asp | Thr | Gln | Tyr  | Phe | Leu | Tyr | Tyr  | Arg | Phe | Gly | Val | Leu | Thr  | Glu |
| 145 |     |     |     | 150  |     |     |     |      | 155 |     |     |     |     |      | 160 |
| Lys | Cys | Gln | Glu | Tyr  | Ser | Arg | Asp | Ala  | Leu | Asn | Arg | Asn | Thr | Ala  | Cys |
|     |     |     |     | 165  |     |     |     |      | 170 |     |     |     |     | 175  |     |
| Trp | Phe | Pro | Arg | Thr  | Phe | Ile | Asn | Ser  | Lys | Gly | Phe | Glu | Gln | Leu  | Ala |
|     |     |     | 180 |      |     |     |     | 185  |     |     |     |     |     | 190  |     |
| Val | His | Ile | Asn | Gly  | Ser | Ser | Lys | Arg  | Ala | Ala | Ile | Lys | Pro | Phe  | Asp |
|     |     | 195 |     |      |     |     | 200 |      |     |     |     | 205 |     |      |     |
| Gln | Leu | Phe | Ser | Pro  | Leu | Ala | Ile | Asp  | Gln | Val | Asn | Pro | Pro | Arg  | Asn |
|     | 210 |     |     |      |     | 215 |     |      |     |     | 220 |     |     |      |     |
| Val | Thr | Val | Glu | Ile  | Glu | Ser | Asn | Ser  | Leu | Tyr | Ile | Gln | Trp | Glu  | Lys |
| 225 |     |     |     | 230  |     |     |     |      | 235 |     |     |     |     |      | 240 |
| Pro | Leu | Ser | Ala | Phe  | Pro | Asp | His | Cys  | Phe | Asn | Tyr | Glu | Leu | Lys  | Ile |
|     |     |     |     | 245  |     |     |     |      | 250 |     |     |     |     | 255  |     |
| Tyr | Asn | Thr | Lys | Asn  | Gly | His | Ile | Gln  | Lys | Glu | Lys | Leu | Ile | Ala  | Asn |
|     |     |     |     | 260  |     |     |     | 265  |     |     |     |     |     | 270  |     |
| Lys | Phe | Ile | Ser | Lys  | Ile | Asp | Asp | Val  | Ser | Thr | Tyr | Ser | Ile | Gln  | Val |
|     |     | 275 |     |      |     |     | 280 |      |     |     |     | 285 |     |      |     |
| Arg | Ala | Ala | Val | Ser  | Ser | Pro | Cys | Arg  | Met | Pro | Gly | Arg | Trp | Gly  | Glu |
|     | 290 |     |     |      |     | 295 |     |      |     |     | 300 |     |     |      |     |
| Trp | Ser | Gln | Pro | Ile  | Tyr | Val | Glu | Thr  | Phe | Glu |     |     |     |      |     |
| 305 |     |     |     | 310  |     |     |     |      |     | 315 |     |     |     |      |     |

( 2 ) INFORMATION FOR SEQ ID NO:9:

( i ) SEQUENCE CHARACTERISTICS:
        ( A ) LENGTH: 1260 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:9:

```
ATGATCATCG TGGCGCATGT ATTACTCATC CTTTTGGGGG CCACTGAGAT ACTGCAAGCT      60
GACTTACTTC CTGATGAAAA GATTTCACTT CTCCCACCTG TCAATTTCAC CATTAAAGTT     120
ACTGGTTTGG CTCAAGTTCT TTTACAATGG AAACCAAATC CTGATCAAGA GCAAAGGAAT     180
GTTAATCTAG AATATCAAGT GAAAATAAAC GCTCCAAAAG AAGATGACTA TGAAACCAGA     240
ATCACTGAAA GCAAATGTGT AACCATCCTC CACAAGGCT  TTTCAGCAAG TGTGCGGACC     300
ATCCTGCAGA ACGACCACTC ACTACTGGCC AGCAGCTGGG CTTCTGCTGA ACTTCATGCC     360
CCACCAGGGT CTCCTGGAAC CTCAGTTGTG AATTTAACTT GCACCACAAA CACTACAGAA     420
GACAATTATT CACGTTTAAG GTCATACCAA GTTTCCCTTC ACTGCACCTG GCTTGTTGGC     480
ACAGATGCCC CTGAGGACAC GCAGTATTTT CTCTACTATA GGTATGGCTC TTGGACTGAA     540
GAATGCCAAG AATACAGCAA AGACACACTG GGGAGAAATA TCGCATGCTG GTTTCCCAGG     600
ACTTTTATCC TCAGCAAAGG GCGTGACTGG CTTGCGGTGC TTGTTAACGG CTCCAGCAAG     660
```

| | | | | | |
|---|---|---|---|---|---|
| CACTCTGCTA | TCAGGCCCTT | TGATCAGCTG | TTTGCCCTTC | ACGCCATTGA | TCAAATAAAT | 720
| CCTCCACTGA | ATGTCACAGC | AGAGATTGAA | GGAACTCGTC | TCTCTATCCA | ATGGGAGAAA | 780
| CCAGTGTCTG | CTTTTCCAAT | CCATTGCTTT | GATTATGAAG | TAAAAATACA | CAATACAAGG | 840
| AATGGATATT | TGCAGATAGA | AAAATTGATG | ACCAATGCAT | TCATCTCAAT | AATTGATGAT | 900
| CTTTCTAAGT | ACGATGTTCA | AGTGAGAGCA | GCAGTGAGCT | CCATGTGCAG | AGAGGCAGGG | 960
| CTCTGGAGTG | AGTGGAGCCA | ACCTATTTAT | GTGGGAAATG | ATGAACACAA | GCCCTTGAGA | 1020
| GAGTGGTTTG | TCATTGTGAT | TATGGCAACC | ATCTGCTTCA | TCTTGTTAAT | TCTCTCGCTT | 1080
| ATCTGTAAAA | TATGTCATTT | ATGGATCAAG | TTGTTTCCAC | CAATTCCAGC | ACCAAAAGT | 1140
| AATATCAAAG | ATCTCTTTGT | AACCACTAAC | TATGAGAAAG | CTGGGTCCAG | TGAGACGGAA | 1200
| ATTGAAGTCA | TCTGTTATAT | AGAGAAGCCT | GGAGTTGAGA | CCCTGGAGGA | TTCTGTGTTT | 1260

(2) INFORMATION FOR SEQ ID NO:10:

( i ) SEQUENCE CHARACTERISTICS:
        ( A ) LENGTH: 2006 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

| | | | | | |
|---|---|---|---|---|---|
| CGGTCCTCGC | CATCTTCTGT | TGAGTACTGG | TCGGAACAAG | AGGATCGTCT | GTAGACAGGA | 60
| TATGATCATC | GTGGCGCATG | TATTACTCAT | CCTTTTGGGG | GCCACTGAGA | TACTGCAAGC | 120
| TGACTTACTT | CCTGATGAAA | AGATTTCACT | TCTCCCACCT | GTCAATTTCA | CCATTAAAGT | 180
| TACTGGTTTG | GCTCAAGTTC | TTTTACAATG | GAAACCAAAT | CCTGATCAAG | AGCAAAGGAA | 240
| TGTTAATCTA | GAATATCAAG | TGAAAATAAA | CGCTCCAAAA | GAAGATGACT | ATGAAACCAG | 300
| AATCACTGAA | AGCAAATGTG | TAACCATCCT | CCACAAAGGC | TTTTCAGCAA | GTGTGCGGAC | 360
| CATCCTGCAG | AACGACCACT | CACTACTGGC | CAGCAGCTGG | GCTTCTGCTG | AACTTCATGC | 420
| CCCACCAGGG | TCTCCTGGAA | CCTCAGTTGT | GAATTTAACT | TGCACCACAA | ACACTACAGA | 480
| AGACAATTAT | TCACGTTTAA | GGTCATACCA | AGTTCCCTT | CACTGCACCT | GGCTTGTTGG | 540
| CACAGATGCC | CCTGAGGACA | CGCAGTATTT | TCTCTACTAT | AGGTATGGCT | CTTGGACTGA | 600
| AGAATGCCAA | GAATACAGCA | AGACACACT | GGGGAGAAAT | ATCGCATGCT | GGTTTCCCAG | 660
| GACTTTTATC | CTCAGCAAAG | GGCGTGACTG | GCTTGCGGTG | CTTGTTAACG | GCTCCAGCAA | 720
| GCACTCTGCT | ATCAGGCCCT | TGATCAGCT | GTTTGCCCTT | CACGCCATTG | ATCAAATAAA | 780
| TCCTCCACTG | AATGTCACAG | CAGAGATTGA | AGGAACTCGT | CTCTCTATCC | AATGGGAGAA | 840
| ACCAGTGTCT | GCTTTTCCAA | TCCATTGCTT | TGATTATGAA | GTAAAAATAC | ACAATACAAG | 900
| GAATGGATAT | TTGCAGATAG | AAAAATTGAT | GACCAATGCA | TTCATCTCAA | TAATTGATGA | 960
| TCTTTCTAAG | TACGATGTTC | AAGTGAGAGC | AGCAGTGAGC | TCCATGTGCA | GAGAGGCAGG | 1020
| GCTCTGGAGT | GAGTGGAGCC | AACCTATTTA | TGTGGGAAAT | GATGAACACA | AGCCCTTGAG | 1080
| AGAGTGGTTT | GTCATTGTGA | TTATGGCAAC | CATCTGCTTC | ATCTTGTTAA | TTCTCTCGCT | 1140
| TATCTGTAAA | ATATGTCATT | TATGGATCAA | GTTGTTTCCA | CCAATTCCAG | CACCAAAAAG | 1200
| TAATATCAAA | GATCTCTTTG | TAACCACTAA | CTATGAGAAA | GCTGGGTCCA | GTGAGACGGA | 1260
| AATTGAAGTC | ATCTGTTATA | TAGAGAAGCC | TGGAGTTGAG | ACCCTGGAGG | ATTCTGTGTT | 1320
| TTGACTGTCA | CTTTGGCATC | CTCTGATGAA | CTCACACATG | CCTCAGTGCC | TCAGTGAAAA | 1380

| | | | | | |
|---|---|---|---|---|---|
| GAACAGGGAT | GCTGGCTCTT | GGCTAAGAGG | TGTTCAGAAT | TTAGGCAACA | CTCAATTTAC | 1440 |
| CTGCGAAGCA | ATACACCCAG | ACACACCAGT | CTTGTATCTC | TTAAAAGTAT | GGATGCTTCA | 1500 |
| TCCAAATCGC | CTCACCTACA | GCAGGGAAGT | TGACTCATCC | AAGCATTTTG | CCATGTTTTT | 1560 |
| TCTCCCCATG | CCGTACAGGG | TAGCACCTCC | TCACCTGCCA | ATCTTTGCAA | TTTGCTTGAC | 1620 |
| TCACCTCAGA | CTTTTCATTC | ACAACAGACA | GCTTTTAAGG | CTAACGTCCA | GCTGTATTTA | 1680 |
| CTTCTGGCTG | TGCCCGTTTG | GCTGTTTAAG | CTGCCAATTG | TAGCACTCAG | CTACCATCTG | 1740 |
| AGGAAGAAAG | CATTTTGCAT | CAGCCTGGAG | TGAATCATGA | ACTTGGATTC | AAGACTGTCT | 1800 |
| TTTCTATAGC | AAGTGAGAGC | CACAAATTCC | TCACCCCCT | ACATTCTAGA | ATGATCTTTT | 1860 |
| TCTAGGTAGA | TTGTGTATGT | GTGTGTATGA | GAGAGAGAGA | GAGAGAGAGA | GAGAGAGAGA | 1920 |
| GAGAAATTAT | CTCAAGCTCC | AGAGGCCTGA | TCCAGGATAC | ATCATTTGAA | ACCAACTAAT | 1980 |
| TTAAAAGCAT | AATAGAGCTA | ATATAT | | | | 2006 |

( 2 ) INFORMATION FOR SEQ ID NO:11:

( i ) SEQUENCE CHARACTERISTICS:
( A ) LENGTH: 1188 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:11:

| | | | | | |
|---|---|---|---|---|---|
| ATGATCATCG | TGGCGCATGT | ATTACTCATC | CTTTTGGGGG | CCACTGAGAT | ACTGCAAGCT | 60 |
| GACTTACTTC | CTGATGAAAA | GATTTCACTT | CTCCCACCTG | TCAATTTCAC | CATTAAAGTT | 120 |
| ACTGGTTTGG | CTCAAGTTCT | TTTACAATGG | AAACCAAATC | CTGATCAAGA | GCAAAGGAAT | 180 |
| GTTAATCTAG | AATATCAAGT | GAAAATAAAC | GCTCCAAAAG | AAGATGACTA | TGAAACCAGA | 240 |
| ATCACTGAAA | GCAAATGTGT | AACCATCCTC | CACAAAGGCT | TTTCAGCAAG | TGTGCGGACC | 300 |
| ATCCTGCAGA | ACGACCACTC | ACTACTGGCC | AGCAGCTGGG | CTTCTGCTGA | ACTTCATGCC | 360 |
| CCACCAGGGT | CTCCTGGAAC | CTCAATTGTG | AATTTAACTT | GCACCACAAA | CACTACAGAA | 420 |
| GACAATTATT | CACGTTTAAG | GTCATACCAA | GTTTCCCTTC | ACTGCACCTG | GCTTGTTGGC | 480 |
| ACAGATGCCC | CTGAGGACAC | GCAGTATTTT | CTCTACTATA | GGTATGGCTC | TTGGACTGAA | 540 |
| GAATGCCAAG | AATACAGCAA | AGACACACTG | GGGAGAAATA | TCGCATGCTG | GTTTCCCAGG | 600 |
| ACTTTTATCC | TCAGCAAAGG | GCGTGACTGG | CTTGCGGTGC | TTGTTAACGG | CTCCAGCAAG | 660 |
| CACTCTGCTA | TCAGGCCCTT | TGATCAGCTG | TTTGCCCTTC | ACGCCATTGA | TCAAATAAAT | 720 |
| CCTCCACTGA | ATGTCACAGC | AGAGATTGAA | GGAACTCGTC | TCTCTATCCA | ATGGGAGAAA | 780 |
| CCAGTGTCTG | CTTTTCCAAT | CCATTGCTTT | GATTATGAAG | TAAAAATACA | CAATACAAGG | 840 |
| AATGGATATT | TGCAGATAGA | AAAATTGATG | ACCAATGCAT | TCATCTCAAT | AATTGATGAT | 900 |
| CTTTCTAAGT | ACGATGTTCA | AGTGAGAGCA | GCAGTGAGCT | CCATGTGCAG | AGAGGCAGGG | 960 |
| CTCTGGAGTG | AGTGGAGCCA | ACCTATTTAT | GTGGGAAATG | ATGAACACAA | GCCCTTGAGA | 1020 |
| GAGTGGTTTG | TCATTGTGAT | TATGGCAACC | ATCTGCTTCA | TCTTGTTAAT | TCTCTCGCTT | 1080 |
| ATCTGTAAAA | TATGTCATTT | ATGGATCAAG | TTGTTTCCAC | CAATTCCAGC | ACCAAAAAGT | 1140 |
| AATATCAAAG | ATCTCTTTGT | AACCACTAAC | TATGAGAAAG | CTGGAATT | | 1188 |

( 2 ) INFORMATION FOR SEQ ID NO:12:

( i ) SEQUENCE CHARACTERISTICS:
    ( A ) LENGTH: 2024 base pairs
    ( B ) TYPE: nucleic acid
    ( C ) STRANDEDNESS: single
    ( D ) TOPOLOGY: linear ( i i ) MOLECULE TYPE: cDNA ( x i ) SEQUENCE DESCRIPTION: SEQ ID NO:12:

```
TAGATGCTGG GGTTGCAGCC ACGAGCATAG ACACGACAGA CACGGTCCTC GCCATCTTCT      60
GTTGAGTACT GGTCGGAACA AGAGGATCGT CTGTAGACAG GATATGATCA TCGTGGCGCA     120
TGTATTACTC ATCCTTTTGG GGGCCACTGA GATACTGCAA GCTGACTTAC TTCCTGATGA     180
AAAGATTTCA CTTCTCCCAC CTGTCAATTT CACCATTAAA GTTACTGGTT TGGCTCAAGT     240
TCTTTTACAA TGGAAACCAA ATCCTGATCA AGAGCAAAGG AATGTTAATC TAGAATATCA     300
AGTGAAAATA AACGCTCCAA AGAAGATGA  CTATGAAACC AGAATCACTG AAAGCAAATG     360
TGTAACCATC CTCCACAAAG GCTTTTCAGC AAGTGTGCGG ACCATCCTGC AGAACGACCA     420
CTCACTACTG GCCAGCAGCT GGGCTTCTGC TGAACTTCAT GCCCCACCAG GGTCTCCTGG     480
AACCTCAATT GTGAATTTAA CTTGCACCAC AAACACTACA GAAGACAATT ATTCACGTTT     540
AAGGTCATAC CAAGTTTCCC TTCACTGCAC CTGGCTTGTT GGCACAGATG CCCCTGAGGA     600
CACGCAGTAT TTTCTCTACT ATAGGTATGG CTCTTGGACT GAAGAATGCC AAGAATACAG     660
CAAAGACACA CTGGGGAGAA ATATCGCATG CTGGTTTCCC AGGACTTTTA TCCTCAGCAA     720
AGGGCGTGAC TGGCTTGCGG TGCTTGTTAA CGGCTCCAGC AAGCACTCTG CTATCAGGCC     780
CTTTGATCAG CTGTTTGCCC TTCACGCCAT TGATCAAATA AATCCTCCAC TGAATGTCAC     840
AGCAGAGATT GAAGGAACTC GTCTCTCTAT CCAATGGGAG AAACCAGTGT CTGCTTTTCC     900
AATCCATTGC TTTGATTATG AAGTAAAAAT ACACAATACA AGGAATGGAT ATTTGCAGAT     960
AGAAAAATTG ATGACCAATG CATTCATCTC AATAATTGAT GATCTTTCTA AGTACGATGT    1020
TCAAGTGAGA GCAGCAGTGA GCTCCATGTG CAGAGAGGCA GGGCTCTGGA GTGAGTGGAG    1080
CCAACCTATT TATGTGGGAA ATGATGAACA CAAGCCCTTG AGAGAGTGGT TTGTCATTGT    1140
GATTATGGCA ACCATCTGCT TCATCTTGTT AATTCTCTCG CTTATCTGTA AAATATGTCA    1200
TTTATGGATC AAGTTGTTTC CACCAATTCC AGCACCAAAA AGTAATATCA AAGATCTCTT    1260
TGTAACCACT AACTATGAGA AAGCTGGAAT TTAAATTCAA GCATGTTTTA ACTTTTGGTT    1320
TAAGGTACTT GGGTGTACCT GGCAGTGTTG TAAGCTCTTT ACATTAATTA ATTAACTCTC    1380
TAGGTACTGT TATCTTCATT TTATAAACAA GGCAGCTGAA GTTGAGAGAA ATAAGTAACC    1440
TGTCCTAGGT CACACAATTA GGAAATGACA GATCTGGCAG TCTATTTCCA GGCAGTCTAT    1500
TTCCACGAGG TCATGAGTGC GAAAGAGGGA CTAGGGAAG  AATGATTAAC TCCAGGGAGC    1560
TGACTTTTCT AGTGTGCTTA CCTGTTTTGC ATCTCTCAAG GATGTGCCAT GAAGCTGTAG    1620
CCAGGTGGAA TTGTACCACA GCCCTGACAT GAACACCTGA TGGCAGCTGC TGGGTTGGAG    1680
CCTAGACAAA AACATGAAGA ACCATGGCTG CTGCCTGAGC CATCGTGCT  GTAATTATAG    1740
AAAACCTTCT AAGGGAAGAA TATGCTGATA TTTTTCAGAT AAGTACCCCT TTTATAAAAA    1800
TCCTCCAAGT TAGCCCTCGA TTTTCCATGT AAGGAAACAG AGGCTTTGAG ATAATGTCTG    1860
TCTCCTAAGG GACAAAGCCA GGACTTGATC CTGTCTTAAA AATGCAAAAT GTAGTACTTC    1920
TTCCATCAAA GGTAGACATG CACTAAGGGA CAGGTTTTGG CTTGGTATCA GAATACATTT    1980
TTAAAAGCTG TGTAAGAATT GAACGGGCTG TACTAGGGGG TATA                     2024
```

( 2 ) INFORMATION FOR SEQ ID NO:13:

( i ) SEQUENCE CHARACTERISTICS:
        ( A ) LENGTH: 420 amino acids
        ( B ) TYPE: amino acid
        ( C ) STRANDEDNESS: unknown
        ( D ) TOPOLOGY: linear ( i i ) MOLECULE TYPE: peptide ( x i ) SEQUENCE DESCRIPTION: SEQ ID NO:13:

```
Met  Ile  Ile  Val  Ala  His  Val  Leu  Leu  Ile  Leu  Leu  Gly  Ala  Thr  Glu
 1                    5                        10                            15

Ile  Leu  Gln  Ala  Asp  Leu  Leu  Pro  Asp  Glu  Lys  Ile  Ser  Leu  Leu  Pro
                20                       25                       30

Pro  Val  Asn  Phe  Thr  Ile  Lys  Val  Thr  Gly  Leu  Ala  Gln  Val  Leu  Leu
           35                       40                       45

Gln  Trp  Lys  Pro  Asn  Pro  Asp  Gln  Glu  Gln  Arg  Asn  Val  Asn  Leu  Glu
      50                       55                       60

Tyr  Gln  Val  Lys  Ile  Asn  Ala  Pro  Lys  Glu  Asp  Asp  Tyr  Glu  Thr  Arg
65                       70                       75                       80

Ile  Thr  Glu  Ser  Lys  Cys  Val  Thr  Ile  Leu  His  Lys  Gly  Phe  Ser  Ala
                85                       90                       95

Ser  Val  Arg  Thr  Ile  Leu  Gln  Asn  Asp  His  Ser  Leu  Leu  Ala  Ser  Ser
                100                      105                      110

Trp  Ala  Ser  Ala  Glu  Leu  His  Ala  Pro  Pro  Gly  Ser  Pro  Gly  Thr  Ser
           115                      120                      125

Val  Val  Asn  Leu  Thr  Cys  Thr  Thr  Asn  Thr  Thr  Glu  Asp  Asn  Tyr  Ser
     130                      135                      140

Arg  Leu  Arg  Ser  Tyr  Gln  Val  Ser  Leu  His  Cys  Thr  Trp  Leu  Val  Gly
145                      150                      155                      160

Thr  Asp  Ala  Pro  Glu  Asp  Thr  Gln  Tyr  Phe  Leu  Tyr  Tyr  Arg  Tyr  Gly
                165                      170                      175

Ser  Trp  Thr  Glu  Glu  Cys  Gln  Glu  Tyr  Ser  Lys  Asp  Thr  Leu  Gly  Arg
                180                      185                      190

Asn  Ile  Ala  Cys  Trp  Phe  Pro  Arg  Thr  Phe  Ile  Leu  Ser  Lys  Gly  Arg
           195                      200                      205

Asp  Trp  Leu  Ala  Val  Leu  Val  Asn  Gly  Ser  Ser  Lys  His  Ser  Ala  Ile
     210                      215                      220

Arg  Pro  Phe  Asp  Gln  Leu  Phe  Ala  Leu  His  Ala  Ile  Asp  Gln  Ile  Asn
225                      230                      235                      240

Pro  Pro  Leu  Asn  Val  Thr  Ala  Glu  Ile  Glu  Gly  Thr  Arg  Leu  Ser  Ile
                245                      250                      255

Gln  Trp  Glu  Lys  Pro  Val  Ser  Ala  Phe  Pro  Ile  His  Cys  Phe  Asp  Tyr
                260                      265                      270

Glu  Val  Lys  Ile  His  Asn  Thr  Arg  Asn  Gly  Tyr  Leu  Gln  Ile  Glu  Lys
           275                      280                      285

Leu  Met  Thr  Asn  Ala  Phe  Ile  Ser  Ile  Ile  Asp  Asp  Leu  Ser  Lys  Tyr
     290                      295                      300

Asp  Val  Gln  Val  Arg  Ala  Ala  Val  Ser  Ser  Met  Cys  Arg  Glu  Ala  Gly
305                      310                      315                      320

Leu  Trp  Ser  Glu  Trp  Ser  Gln  Pro  Ile  Tyr  Val  Gly  Asn  Asp  Glu  His
                325                      330                      335

Lys  Pro  Leu  Arg  Glu  Trp  Phe  Val  Ile  Val  Ile  Met  Ala  Thr  Ile  Cys
                340                      345                      350

Phe  Ile  Leu  Leu  Ile  Leu  Ser  Leu  Ile  Cys  Lys  Ile  Cys  His  Leu  Trp
```

|   |   |   |   |   | 355 |   |   |   |   | 360 |   |   |   |   | 365 |   |   |   |
|---|---|---|---|---|---|---|---|---|---|---|---|---|---|---|---|---|---|---|

Ile Lys Leu Phe Pro Pro Ile Pro Ala Pro Lys Ser Asn Ile Lys Asp
    370                  375                  380

Leu Phe Val Thr Thr Asn Tyr Glu Lys Ala Gly Ser Ser Glu Thr Glu
385                      390                  395                400

Ile Glu Val Ile Cys Tyr Ile Glu Lys Pro Gly Val Glu Thr Leu Glu
                405                  410                  415

Asp Ser Val Phe
          420

(2) INFORMATION FOR SEQ ID NO:14:

(i) SEQUENCE CHARACTERISTICS:
    (A) LENGTH: 396 amino acids
    (B) TYPE: amino acid
    (C) STRANDEDNESS: unknown
    (D) TOPOLOGY: linear (ii) MOLECULE TYPE: peptide (xi) SEQUENCE DESCRIPTION: SEQ ID NO:14:

Met Ile Ile Val Ala His Val Leu Leu Ile Leu Leu Gly Ala Thr Glu
1                5                  10                  15

Ile Leu Gln Ala Asp Leu Leu Pro Asp Glu Lys Ile Ser Leu Leu Pro
           20                  25                  30

Pro Val Asn Phe Thr Ile Lys Val Thr Gly Leu Ala Gln Val Leu Leu
           35                  40                  45

Gln Trp Lys Pro Asn Pro Asp Gln Glu Gln Arg Asn Val Asn Leu Glu
      50                  55                  60

Tyr Gln Val Lys Ile Asn Ala Pro Lys Glu Asp Asp Tyr Glu Thr Arg
65                      70                  75                80

Ile Thr Glu Ser Lys Cys Val Thr Ile Leu His Lys Gly Phe Ser Ala
                85                  90                  95

Ser Val Arg Thr Ile Leu Gln Asn Asp His Ser Leu Leu Ala Ser Ser
           100                  105                110

Trp Ala Ser Ala Glu Leu His Ala Pro Pro Gly Ser Pro Gly Thr Ser
           115                  120                125

Ile Val Asn Leu Thr Cys Thr Thr Asn Thr Thr Glu Asp Asn Tyr Ser
     130                  135                  140

Arg Leu Arg Ser Tyr Gln Val Ser Leu His Cys Thr Trp Leu Val Gly
145                    150                  155                160

Thr Asp Ala Pro Glu Asp Thr Gln Tyr Phe Leu Tyr Tyr Arg Tyr Gly
                  165                  170                175

Ser Trp Thr Glu Glu Cys Gln Glu Tyr Ser Lys Asp Thr Leu Gly Arg
             180                  185                190

Asn Ile Ala Cys Trp Phe Pro Arg Thr Phe Ile Leu Ser Lys Gly Arg
         195                  200                205

Asp Trp Leu Ala Val Leu Val Asn Gly Ser Ser Lys His Ser Ala Ile
     210                215                220

Arg Pro Phe Asp Gln Leu Phe Ala Leu His Ala Ile Asp Gln Ile Asn
225                    230                235                240

Pro Pro Leu Asn Val Thr Ala Glu Ile Glu Gly Thr Arg Leu Ser Ile
              245                  250                255

Gln Trp Glu Lys Pro Val Ser Ala Phe Pro Ile His Cys Phe Asp Tyr
         260                  265                270

Glu Val Lys Ile His Asn Thr Arg Asn Gly Tyr Leu Gln Ile Glu Lys

|   |   |   | 275 |   |   |   |   | 280 |   |   |   |   | 285 |   |   |
|---|---|---|---|---|---|---|---|---|---|---|---|---|---|---|---|
| Leu | Met | Thr | Asn | Ala | Phe | Ile | Ser | Ile | Ile | Asp | Asp | Leu | Ser | Lys | Tyr |
|  | 290 |   |   |   |   | 295 |   |   |   | 300 |   |   |   |   |   |
| Asp | Val | Gln | Val | Arg | Ala | Ala | Val | Ser | Ser | Met | Cys | Arg | Glu | Ala | Gly |
| 305 |   |   |   |   | 310 |   |   |   |   | 315 |   |   |   |   | 320 |
| Leu | Trp | Ser | Glu | Trp | Ser | Gln | Pro | Ile | Tyr | Val | Gly | Asn | Asp | Glu | His |
|  |   |   |   | 325 |   |   |   |   | 330 |   |   |   |   | 335 |   |
| Lys | Pro | Leu | Arg | Glu | Trp | Phe | Val | Ile | Val | Ile | Met | Ala | Thr | Ile | Cys |
|  |   |   | 340 |   |   |   |   | 345 |   |   |   | 350 |   |   |   |
| Phe | Ile | Leu | Leu | Ile | Leu | Ser | Leu | Ile | Cys | Lys | Ile | Cys | His | Leu | Trp |
|  |   |   | 355 |   |   |   |   | 360 |   |   |   | 365 |   |   |   |
| Ile | Lys | Leu | Phe | Pro | Pro | Ile | Pro | Ala | Pro | Lys | Ser | Asn | Ile | Lys | Asp |
|  |   | 370 |   |   |   |   | 375 |   |   |   |   | 380 |   |   |   |
| Leu | Phe | Val | Thr | Thr | Asn | Tyr | Glu | Lys | Ala | Gly | Ile |   |   |   |   |
| 385 |   |   |   |   | 390 |   |   |   |   | 395 |   |   |   |   |   |

( 2 ) INFORMATION FOR SEQ ID NO:15:

( i ) SEQUENCE CHARACTERISTICS:
        ( A ) LENGTH: 1808 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 303..1547

( x i ) SEQUENCE DESCRIPTION: SEQ ID NO:15:

```
GAAATAATTG  GTAAACACAG  AAAATGTTTC  AATAGAAAAA  AGAGGAAACA  GAACACTGTG      60

TAGCCCTGTT  ATCAGCAGAG  ACAGAGCTAA  CGCTGGGGAT  ACCAAACTAG  AAGAAGCTCA     120

CTGGACAGGT  CCCGGTATGC  AGTTCTATTT  TTGTTGATGG  CTCTGTATCT  AATGTGTTCA     180

TTTGTACCAA  GGATCTAACC  AGGGTCTTCC  AGAGTCTGAG  CAAGCTTCTC  CCACTGAGCT     240

ACATCACAGC  CCCTGTTTA   TTGGAAGAAG  AAATACTTAC  ACCTTTCCAG  TATTCGGCTA     300
```

| CC | ATG | GTG | CCT | GTG | TTA | CTA | ATT | CTT | GTG | GGA | GCT | TTG | GCA | ACA | CTG | 347 |
|---|---|---|---|---|---|---|---|---|---|---|---|---|---|---|---|---|
|   | Met | Val | Pro | Val | Leu | Leu | Ile | Leu | Val | Gly | Ala | Leu | Ala | Thr | Leu |   |
|   | 1 |   |   |   | 5 |   |   |   |   | 10 |   |   |   |   | 15 |   |

| CAA | GCT | GAC | TTA | CTT | AAT | CAC | AAA | AAG | TTT | TTA | CTT | CTA | CCA | CCT | GTC | 395 |
|---|---|---|---|---|---|---|---|---|---|---|---|---|---|---|---|---|
| Gln | Ala | Asp | Leu | Leu | Asn | His | Lys | Lys | Phe | Leu | Leu | Leu | Pro | Pro | Val |   |
|   |   |   |   | 20 |   |   |   |   | 25 |   |   |   |   | 30 |   |   |

| AAT | TTT | ACC | ATT | AAA | GCC | ACT | GGA | TTA | GCT | CAA | GTT | CTT | TTA | CAC | TGG | 443 |
|---|---|---|---|---|---|---|---|---|---|---|---|---|---|---|---|---|
| Asn | Phe | Thr | Ile | Lys | Ala | Thr | Gly | Leu | Ala | Gln | Val | Leu | Leu | His | Trp |   |
|   |   |   | 35 |   |   |   |   | 40 |   |   |   |   | 45 |   |   |   |

| GAC | CCA | AAT | CCT | GAC | CAA | GAG | CAA | AGG | CAT | GTT | GAT | CTA | GAG | TAT | CAC | 491 |
|---|---|---|---|---|---|---|---|---|---|---|---|---|---|---|---|---|
| Asp | Pro | Asn | Pro | Asp | Gln | Glu | Gln | Arg | His | Val | Asp | Leu | Glu | Tyr | His |   |
|   |   | 50 |   |   |   |   | 55 |   |   |   |   | 60 |   |   |   |   |

| GTG | AAA | ATA | AAT | GCC | CCA | CAA | GAA | GAC | GAA | TAT | GAT | ACC | AGA | AAG | ACT | 539 |
|---|---|---|---|---|---|---|---|---|---|---|---|---|---|---|---|---|
| Val | Lys | Ile | Asn | Ala | Pro | Gln | Glu | Asp | Glu | Tyr | Asp | Thr | Arg | Lys | Thr |   |
|   | 65 |   |   |   |   | 70 |   |   |   |   | 75 |   |   |   |   |   |

| GAA | AGC | AAA | TGT | GTG | ACC | CCC | CTT | CAT | GAA | GGC | TTT | GCA | GCT | AGC | GTG | 587 |
|---|---|---|---|---|---|---|---|---|---|---|---|---|---|---|---|---|
| Glu | Ser | Lys | Cys | Val | Thr | Pro | Leu | His | Glu | Gly | Phe | Ala | Ala | Ser | Val |   |
| 80 |   |   |   |   | 85 |   |   |   |   | 90 |   |   |   |   | 95 |   |

| AGG | ACC | ATT | CTG | AAG | AGC | AGC | CAT | ACA | ACT | CTG | GCC | AGC | AGT | TGG | GTT | 635 |
|---|---|---|---|---|---|---|---|---|---|---|---|---|---|---|---|---|
| Arg | Thr | Ile | Leu | Lys | Ser | Ser | His | Thr | Thr | Leu | Ala | Ser | Ser | Trp | Val |   |
|   |   |   |   | 100 |   |   |   |   | 105 |   |   |   |   | 110 |   |   |

| TCT | GCT | GAA | CTC | AAA | GCT | CCA | CCA | GGA | TCT | CCT | GGA | ACC | TCG | GTT | ACG | 683 |
|---|---|---|---|---|---|---|---|---|---|---|---|---|---|---|---|---|

```
Ser Ala Glu Leu Lys Ala Pro Pro Gly Ser Pro Gly Thr Ser Val Thr
        115             120             125

AAT TTA ACT TGT ACC ACA CAC ACT GTT GTA AGT AGC CAC ACC CAC TTA    731
Asn Leu Thr Cys Thr Thr His Thr Val Val Ser Ser His Thr His Leu
        130             135             140

AGG CCA TAC CAA GTG TCC CTT CGT TGC ACC TGG CTT GTT GGG AAG GAT    779
Arg Pro Tyr Gln Val Ser Leu Arg Cys Thr Trp Leu Val Gly Lys Asp
        145             150             155

GCC CCT GAG GAC ACA CAG TAT TTC CTA TAC TAC AGG TTT GGT GTT TTG    827
Ala Pro Glu Asp Thr Gln Tyr Phe Leu Tyr Tyr Arg Phe Gly Val Leu
160             165             170             175

ACT GAA AAA TGC CAA GAA TAC AGC AGA GAT GCA CTG AAC AGA AAT ACT    875
Thr Glu Lys Cys Gln Glu Tyr Ser Arg Asp Ala Leu Asn Arg Asn Thr
                180             185             190

GCA TGC TGG TTT CCC AGG ACA TTT ATC AAC AGC AAA GGG TTT GAA CAG    923
Ala Cys Trp Phe Pro Arg Thr Phe Ile Asn Ser Lys Gly Phe Glu Gln
        195             200             205

CTT GCT GTG CAC ATT AAT GGC TCA AGC AAG CGT GCT GCA ATC AAG CCC    971
Leu Ala Val His Ile Asn Gly Ser Ser Lys Arg Ala Ala Ile Lys Pro
        210             215             220

TTT GAT CAG CTG TTC AGT CCA CTT GCC ATT GAC CAA GTG AAT CCT CCA   1019
Phe Asp Gln Leu Phe Ser Pro Leu Ala Ile Asp Gln Val Asn Pro Pro
        225             230             235

AGG AAT GTC ACA GTG GAA ATT GAA AGC AAT TCT CTC TAT ATA CAG TGG   1067
Arg Asn Val Thr Val Glu Ile Glu Ser Asn Ser Leu Tyr Ile Gln Trp
240             245             250             255

GAG AAA CCA CTT TCT GCC TTT CCA GAT CAT TGC TTT AAC TAT GAG CTG   1115
Glu Lys Pro Leu Ser Ala Phe Pro Asp His Cys Phe Asn Tyr Glu Leu
        260             265             270

AAA ATT TAC AAC ACA AAA AAT GGT CAC ATT CAG AAG GAA AAA CTG ATC   1163
Lys Ile Tyr Asn Thr Lys Asn Gly His Ile Gln Lys Glu Lys Leu Ile
        275             280             285

GCC AAT AAG TTC ATC TCA AAA ATT GAT GAT GTT TCT ACA TAT TCC ATT   1211
Ala Asn Lys Phe Ile Ser Lys Ile Asp Asp Val Ser Thr Tyr Ser Ile
        290             295             300

CAA GTG AGA GCA GCT GTG AGC TCA CCT TGC AGA ATG CCA GGA AGG TGG   1259
Gln Val Arg Ala Ala Val Ser Ser Pro Cys Arg Met Pro Gly Arg Trp
        305             310             315

GGC GAG TGG AGT CAA CCT ATT TAT GTG GGA AAG GAA AGG AAG TCC TTG   1307
Gly Glu Trp Ser Gln Pro Ile Tyr Val Gly Lys Glu Arg Lys Ser Leu
320             325             330             335

GTA GAA TGG CAT CTC ATT GTG CTC CCA ACA GCT GCC TGC TTC GTC TTG   1355
Val Glu Trp His Leu Ile Val Leu Pro Thr Ala Ala Cys Phe Val Leu
        340             345             350

TTA ATC TTC TCA CTC ATC TGC AGA GTG TGT CAT TTA TGG ACC AGG TTG   1403
Leu Ile Phe Ser Leu Ile Cys Arg Val Cys His Leu Trp Thr Arg Leu
        355             360             365

TTT CCA CCG GTT CCG GCC CCA AAG AGT AAC ATC AAA GAT CTC CCT GTG   1451
Phe Pro Pro Val Pro Ala Pro Lys Ser Asn Ile Lys Asp Leu Pro Val
        370             375             380

GTT ACT GAA TAT GAG AAA CCT TCG AAT GAA ACC AAA ATT GAA GTT GTA   1499
Val Thr Glu Tyr Glu Lys Pro Ser Asn Glu Thr Lys Ile Glu Val Val
        385             390             395

CAT TGT GTG GAA GAG GTT GGA TTT GAA GTC ATG GGA AAT TCC ACG TTT   1547
His Cys Val Glu Glu Val Gly Phe Glu Val Met Gly Asn Ser Thr Phe
400             405             410             415

TGATGGCATT TTGCCATTCT GAAATGAACT CATACAGGAC TCCGTGATAA GAGCAAGGAC   1607

TGCTATTTCT TGGCAAGGAG GTATTTCAAA TGAACACTCA GAGCCAGGCG GTGGTAGAGC   1667
```

-continued

```
TCGCCTTTAA TACCAGCACC TGGGATGCAC AGACGGGAGG ATTTCTGAGT TCGAGGCCAG      1727

CTTGGTCTAT AAAGTGAGTT CCAGGACAGC CAGAGCTACA CAGAGAAACC CTGTCTCGAA      1787

AAAACAAACA AACAAACAAA C                                                1808
```

( 2 ) INFORMATION FOR SEQ ID NO:16:

( i ) SEQUENCE CHARACTERISTICS:
        ( A ) LENGTH: 1355 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 13..1008

( x i ) SEQUENCE DESCRIPTION: SEQ ID NO:16:

```
TATTCGGCTA CC ATG GTG CCT GTG TTA CTA ATT CTT GTG GGA GCT TTG          48
              Met Val Pro Val Leu Leu Ile Leu Val Gly Ala Leu
                1               5                  10

GCA ACA CTG CAA GCT GAC TTA CTT AAT CAC AAA AAG TTT TTA CTT CTA        96
Ala Thr Leu Gln Ala Asp Leu Leu Asn His Lys Lys Phe Leu Leu Leu
             15                  20                  25

CCA CCT GTC AAT TTT ACC ATT AAA GCC ACT GGA TTA GCT CAA GTT CTT       144
Pro Pro Val Asn Phe Thr Ile Lys Ala Thr Gly Leu Ala Gln Val Leu
     30                  35                  40

TTA CAC TGG GAC CCA AAT CCT GAC CAA GAG CAA AGG CAT GTT GAT CTA       192
Leu His Trp Asp Pro Asn Pro Asp Gln Glu Gln Arg His Val Asp Leu
 45                  50                  55                  60

GAG TAT CAC GTG AAA ATA AAT GCC CCA CAA GAA GAC GAA TAT GAT ACC       240
Glu Tyr His Val Lys Ile Asn Ala Pro Gln Glu Asp Glu Tyr Asp Thr
                 65                  70                  75

AGA AAG ACT GAA AGC AAA TGT GTG ACC CCC CTT CAT GAA GGC TTT GCA       288
Arg Lys Thr Glu Ser Lys Cys Val Thr Pro Leu His Glu Gly Phe Ala
             80                  85                  90

GCT AGC GTG AGG ACC ATT CTG AAG AGC AGC CAT ACA ACT CTG GCC AGC       336
Ala Ser Val Arg Thr Ile Leu Lys Ser Ser His Thr Thr Leu Ala Ser
         95                 100                 105

AGT TGG GTT TCT GCT GAA CTC AAA GCT CCA CCA GGA TCT CCT GGA ACC       384
Ser Trp Val Ser Ala Glu Leu Lys Ala Pro Pro Gly Ser Pro Gly Thr
 110                 115                 120

TCG GTT ACG AAT TTA ACT TGT ACC ACA CAC ACT GTT GTA AGT AGC CAC       432
Ser Val Thr Asn Leu Thr Cys Thr Thr His Thr Val Val Ser Ser His
125                 130                 135                 140

ACC CAC TTA AGG CCA TAC CAA GTG TCC CTT CGT TGC ACC TGG CTT GTT       480
Thr His Leu Arg Pro Tyr Gln Val Ser Leu Arg Cys Thr Trp Leu Val
                145                 150                 155

GGG AAG GAT GCC CCT GAG GAC ACA CAG TAT TTC CTA TAC TAC AGG TTT       528
Gly Lys Asp Ala Pro Glu Asp Thr Gln Tyr Phe Leu Tyr Tyr Arg Phe
            160                 165                 170

GGT GTT TTG ACT GAA AAA TGC CAA GAA TAC AGC AGA GAT GCA CTG AAC       576
Gly Val Leu Thr Glu Lys Cys Gln Glu Tyr Ser Arg Asp Ala Leu Asn
        175                 180                 185

AGA AAT ACT GCA TGC TGG TTT CCC AGG ACA TTT ATC AAC AGC AAA GGG       624
Arg Asn Thr Ala Cys Trp Phe Pro Arg Thr Phe Ile Asn Ser Lys Gly
    190                 195                 200

TTT GAA CAG CTT GCT GTG CAC ATT AAT GGC TCA AGC AAG CGT GCT GCA       672
Phe Glu Gln Leu Ala Val His Ile Asn Gly Ser Ser Lys Arg Ala Ala
205                 210                 215                 220
```

-continued

| | | | | | | | | | | | | | | | | |
|---|---|---|---|---|---|---|---|---|---|---|---|---|---|---|---|---|
| ATC | AAG | CCC | TTT | GAT | CAG | CTG | TTC | AGT | CCA | CTT | GCC | ATT | GAC | CAA | GTG | 720 |
| Ile | Lys | Pro | Phe | Asp | Gln | Leu | Phe | Ser | Pro | Leu | Ala | Ile | Asp | Gln | Val | |
| | | | | 225 | | | | 230 | | | | | 235 | | | |
| AAT | CCT | CCA | AGG | AAT | GTC | ACA | GTG | GAA | ATT | GAA | AGC | AAT | TCT | CTC | TAT | 768 |
| Asn | Pro | Pro | Arg | Asn | Val | Thr | Val | Glu | Ile | Glu | Ser | Asn | Ser | Leu | Tyr | |
| | | | 240 | | | | 245 | | | | | 250 | | | | |
| ATA | CAG | TGG | GAG | AAA | CCA | CTT | TCT | GCC | TTT | CCA | GAT | CAT | TGC | TTT | AAC | 816 |
| Ile | Gln | Trp | Glu | Lys | Pro | Leu | Ser | Ala | Phe | Pro | Asp | His | Cys | Phe | Asn | |
| | | | 255 | | | | 260 | | | | | 265 | | | | |
| TAT | GAG | CTG | AAA | ATT | TAC | AAC | ACA | AAA | AAT | GGT | CAC | ATT | CAG | AAG | GAA | 864 |
| Tyr | Glu | Leu | Lys | Ile | Tyr | Asn | Thr | Lys | Asn | Gly | His | Ile | Gln | Lys | Glu | |
| | 270 | | | | 275 | | | | | 280 | | | | | | |
| AAA | CTG | ATC | GCC | AAT | AAG | TTC | ATC | TCA | AAA | ATT | GAT | GAT | GTT | TCT | ACA | 912 |
| Lys | Leu | Ile | Ala | Asn | Lys | Phe | Ile | Ser | Lys | Ile | Asp | Asp | Val | Ser | Thr | |
| 285 | | | | | 290 | | | | 295 | | | | | 300 | | |
| TAT | TCC | ATT | CAA | GTG | AGA | GCA | GCT | GTG | AGC | TCA | CCT | TGC | AGA | ATG | CCA | 960 |
| Tyr | Ser | Ile | Gln | Val | Arg | Ala | Ala | Val | Ser | Ser | Pro | Cys | Arg | Met | Pro | |
| | | | | 305 | | | | 310 | | | | | 315 | | | |
| GGA | AGG | TGG | GGC | GAG | TGG | AGT | CAA | CCT | ATT | TAT | GTG | GAA | ACC | TTC | GAA | 1008 |
| Gly | Arg | Trp | Gly | Glu | Trp | Ser | Gln | Pro | Ile | Tyr | Val | Glu | Thr | Phe | Glu | |
| | | | 320 | | | | 325 | | | | | 330 | | | | |

| | | | | | |
|---|---|---|---|---|---|
| TGAAACCAAA | ATTGAAGTTG | TACATTGTGT | GGAAGAGGTT | GGATTTGAAG | TCATGGGAAA | 1068 |
| TTCCACGTTT | TGATGGCATT | TTGCCATTCT | GAAATGAACT | CATACAGGAC | TCCGTGATAA | 1128 |
| GAGCAAGGAC | TGCTATTTCT | TGGCAAGGAG | GTATTTCAAA | TGAACACTCA | GAGCCAGGCG | 1188 |
| GTGGTAGAGC | TCGCCTTTAA | TACCAGCACC | TGGGATGCAC | AGACGGGAGG | ATTTCTGAGT | 1248 |
| TCGAGGCCAG | CTTGGTCTAT | AAAGTGAGTT | CCAGGACAGC | CAGAGCTACA | CAGAGAAACC | 1308 |
| CTGTCTCGAA | AAACAAACA | AACAAACAAA | CAAACAAAAA | TGAACAC | | 1355 |

( 2 ) INFORMATION FOR SEQ ID NO:17:

( i ) SEQUENCE CHARACTERISTICS:
        ( A ) LENGTH: 2006 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 62..1324

( x i ) SEQUENCE DESCRIPTION: SEQ ID NO:17:

| | | | | | |
|---|---|---|---|---|---|
| CGGTCCTCGC | CATCTTCTGT | TGAGTACTGG | TCGGAACAAG | AGGATCGTCT | GTAGACAGGA | 60 |

| | | | | | | | | | | | | | | | | |
|---|---|---|---|---|---|---|---|---|---|---|---|---|---|---|---|---|
| T | ATG | ATC | ATC | GTG | GCG | CAT | GTA | TTA | CTC | ATC | CTT | TTG | GGG | GCC | ACT | 106 |
| | Met | Ile | Ile | Val | Ala | His | Val | Leu | Leu | Ile | Leu | Leu | Gly | Ala | Thr | |
| | 1 | | | | 5 | | | | | 10 | | | | | 15 | |
| GAG | ATA | CTG | CAA | GCT | GAC | TTA | CTT | CCT | GAT | GAA | AAG | ATT | TCA | CTT | CTC | 154 |
| Glu | Ile | Leu | Gln | Ala | Asp | Leu | Leu | Pro | Asp | Glu | Lys | Ile | Ser | Leu | Leu | |
| | | | | 20 | | | | 25 | | | | | 30 | | | |
| CCA | CCT | GTC | AAT | TTC | ACC | ATT | AAA | GTT | ACT | GGT | TTG | GCT | CAA | GTT | CTT | 202 |
| Pro | Pro | Val | Asn | Phe | Thr | Ile | Lys | Val | Thr | Gly | Leu | Ala | Gln | Val | Leu | |
| | | | 35 | | | | 40 | | | | | 45 | | | | |
| TTA | CAA | TGG | AAA | CCA | AAT | CCT | GAT | CAA | GAG | CAA | AGG | AAT | GTT | AAT | CTA | 250 |
| Leu | Gln | Trp | Lys | Pro | Asn | Pro | Asp | Gln | Glu | Gln | Arg | Asn | Val | Asn | Leu | |
| | | | 50 | | | | 55 | | | | | 60 | | | | |
| GAA | TAT | CAA | GTG | AAA | ATA | AAC | GCT | CCA | AAA | GAA | GAT | GAC | TAT | GAA | ACC | 298 |
| Glu | Tyr | Gln | Val | Lys | Ile | Asn | Ala | Pro | Lys | Glu | Asp | Asp | Tyr | Glu | Thr | |
| | 65 | | | | 70 | | | | | 75 | | | | | | |

-continued

| | | | | | | | | | | | | | | | | |
|---|---|---|---|---|---|---|---|---|---|---|---|---|---|---|---|---|
| AGA | ATC | ACT | GAA | AGC | AAA | TGT | GTA | ACC | ATC | CTC | CAC | AAA | GGC | TTT | TCA | 346 |
| Arg | Ile | Thr | Glu | Ser | Lys | Cys | Val | Thr | Ile | Leu | His | Lys | Gly | Phe | Ser | |
| 80 | | | | | 85 | | | | | 90 | | | | | 95 | |
| GCA | AGT | GTG | CGG | ACC | ATC | CTG | CAG | AAC | GAC | CAC | TCA | CTA | CTG | GCC | AGC | 394 |
| Ala | Ser | Val | Arg | Thr | Ile | Leu | Gln | Asn | Asp | His | Ser | Leu | Leu | Ala | Ser | |
| | | | | 100 | | | | | 105 | | | | | 110 | | |
| AGC | TGG | GCT | TCT | GCT | GAA | CTT | CAT | GCC | CCA | CCA | GGG | TCT | CCT | GGA | ACC | 442 |
| Ser | Trp | Ala | Ser | Ala | Glu | Leu | His | Ala | Pro | Pro | Gly | Ser | Pro | Gly | Thr | |
| | | | 115 | | | | | 120 | | | | | 125 | | | |
| TCA | GTT | GTG | AAT | TTA | ACT | TGC | ACC | ACA | AAC | ACT | ACA | GAA | GAC | AAT | TAT | 490 |
| Ser | Val | Val | Asn | Leu | Thr | Cys | Thr | Thr | Asn | Thr | Thr | Glu | Asp | Asn | Tyr | |
| | | 130 | | | | | 135 | | | | | 140 | | | | |
| TCA | CGT | TTA | AGG | TCA | TAC | CAA | GTT | TCC | CTT | CAC | TGC | ACC | TGG | CTT | GTT | 538 |
| Ser | Arg | Leu | Arg | Ser | Tyr | Gln | Val | Ser | Leu | His | Cys | Thr | Trp | Leu | Val | |
| | 145 | | | | | 150 | | | | | 155 | | | | | |
| GGC | ACA | GAT | GCC | CCT | GAG | GAC | ACG | CAG | TAT | TTT | CTC | TAC | TAT | AGG | TAT | 586 |
| Gly | Thr | Asp | Ala | Pro | Glu | Asp | Thr | Gln | Tyr | Phe | Leu | Tyr | Tyr | Arg | Tyr | |
| 160 | | | | | 165 | | | | | 170 | | | | | 175 | |
| GGC | TCT | TGG | ACT | GAA | GAA | TGC | CAA | GAA | TAC | AGC | AAA | GAC | ACA | CTG | GGG | 634 |
| Gly | Ser | Trp | Thr | Glu | Glu | Cys | Gln | Glu | Tyr | Ser | Lys | Asp | Thr | Leu | Gly | |
| | | | | 180 | | | | | 185 | | | | | 190 | | |
| AGA | AAT | ATC | GCA | TGC | TGG | TTT | CCC | AGG | ACT | TTT | ATC | CTC | AGC | AAA | GGG | 682 |
| Arg | Asn | Ile | Ala | Cys | Trp | Phe | Pro | Arg | Thr | Phe | Ile | Leu | Ser | Lys | Gly | |
| | | | 195 | | | | | 200 | | | | | 205 | | | |
| CGT | GAC | TGG | CTT | GCG | GTG | CTT | GTT | AAC | GGC | TCC | AGC | AAG | CAC | TCT | GCT | 730 |
| Arg | Asp | Trp | Leu | Ala | Val | Leu | Val | Asn | Gly | Ser | Ser | Lys | His | Ser | Ala | |
| | | 210 | | | | | 215 | | | | | 220 | | | | |
| ATC | AGG | CCC | TTT | GAT | CAG | CTG | TTT | GCC | CTT | CAC | GCC | ATT | GAT | CAA | ATA | 778 |
| Ile | Arg | Pro | Phe | Asp | Gln | Leu | Phe | Ala | Leu | His | Ala | Ile | Asp | Gln | Ile | |
| | 225 | | | | | 230 | | | | | 235 | | | | | |
| AAT | CCT | CCA | CTG | AAT | GTC | ACA | GCA | GAG | ATT | GAA | GGA | ACT | CGT | CTC | TCT | 826 |
| Asn | Pro | Pro | Leu | Asn | Val | Thr | Ala | Glu | Ile | Glu | Gly | Thr | Arg | Leu | Ser | |
| 240 | | | | | 245 | | | | | 250 | | | | | 255 | |
| ATC | CAA | TGG | GAG | AAA | CCA | GTG | TCT | GCT | TTT | CCA | ATC | CAT | TGC | TTT | GAT | 874 |
| Ile | Gln | Trp | Glu | Lys | Pro | Val | Ser | Ala | Phe | Pro | Ile | His | Cys | Phe | Asp | |
| | | | | 260 | | | | | 265 | | | | | 270 | | |
| TAT | GAA | GTA | AAA | ATA | CAC | AAT | ACA | AGG | AAT | GGA | TAT | TTG | CAG | ATA | GAA | 922 |
| Tyr | Glu | Val | Lys | Ile | His | Asn | Thr | Arg | Asn | Gly | Tyr | Leu | Gln | Ile | Glu | |
| | | | 275 | | | | | 280 | | | | | 285 | | | |
| AAA | TTG | ATG | ACC | AAT | GCA | TTC | ATC | TCA | ATA | ATT | GAT | GAT | CTT | TCT | AAG | 970 |
| Lys | Leu | Met | Thr | Asn | Ala | Phe | Ile | Ser | Ile | Ile | Asp | Asp | Leu | Ser | Lys | |
| | | 290 | | | | | 295 | | | | | 300 | | | | |
| TAC | GAT | GTT | CAA | GTG | AGA | GCA | GCA | GTG | AGC | TCC | ATG | TGC | AGA | GAG | GCA | 1018 |
| Tyr | Asp | Val | Gln | Val | Arg | Ala | Ala | Val | Ser | Ser | Met | Cys | Arg | Glu | Ala | |
| | 305 | | | | | 310 | | | | | 315 | | | | | |
| GGG | CTC | TGG | AGT | GAG | TGG | AGC | CAA | CCT | ATT | TAT | GTG | GGA | AAT | GAT | GAA | 1066 |
| Gly | Leu | Trp | Ser | Glu | Trp | Ser | Gln | Pro | Ile | Tyr | Val | Gly | Asn | Asp | Glu | |
| 320 | | | | | 325 | | | | | 330 | | | | | 335 | |
| CAC | AAG | CCC | TTG | AGA | GAG | TGG | TTT | GTC | ATT | GTG | ATT | ATG | GCA | ACC | ATC | 1114 |
| His | Lys | Pro | Leu | Arg | Glu | Trp | Phe | Val | Ile | Val | Ile | Met | Ala | Thr | Ile | |
| | | | | 340 | | | | | 345 | | | | | 350 | | |
| TGC | TTC | ATC | TTG | TTA | ATT | CTC | TCG | CTT | ATC | TGT | AAA | ATA | TGT | CAT | TTA | 1162 |
| Cys | Phe | Ile | Leu | Leu | Ile | Leu | Ser | Leu | Ile | Cys | Lys | Ile | Cys | His | Leu | |
| | | | 355 | | | | | 360 | | | | | 365 | | | |
| TGG | ATC | AAG | TTG | TTT | CCA | CCA | ATT | CCA | GCA | CCA | AAA | AGT | AAT | ATC | AAA | 1210 |
| Trp | Ile | Lys | Leu | Phe | Pro | Pro | Ile | Pro | Ala | Pro | Lys | Ser | Asn | Ile | Lys | |
| | | 370 | | | | | 375 | | | | | 380 | | | | |
| GAT | CTC | TTT | GTA | ACC | ACT | AAC | TAT | GAG | AAA | GCT | GGG | TCC | AGT | GAG | ACG | 1258 |
| Asp | Leu | Phe | Val | Thr | Thr | Asn | Tyr | Glu | Lys | Ala | Gly | Ser | Ser | Glu | Thr | |
| 385 | | | | | 390 | | | | | 395 | | | | | | |

| | | | | | | | | | | | | | | | |
|---|---|---|---|---|---|---|---|---|---|---|---|---|---|---|---|
|GAA|ATT|GAA|GTC|ATC|TGT|TAT|ATA|GAG|AAG|CCT|GGA|GTT|GAG|ACC|CTG|1306
|Glu|Ile|Glu|Val|Ile|Cys|Tyr|Ile|Glu|Lys|Pro|Gly|Val|Glu|Thr|Leu|
|400| | | |405| | | |410| | | |415| | | |

| | | | | | | |
|---|---|---|---|---|---|---|
|GAG|GAT|TCT|GTG|TTT|TGACTGTCAC TTTGGCATCC TCTGATGAAC TCACACATGC|1361
|Glu|Asp|Ser|Val|Phe| | |
| | | |420| | | |

| | | | | |
|---|---|---|---|---|
|CTCAGTGCCT|CAGTGAAAAG|AACAGGGATG|CTGGCTCTTG|GCTAAGAGGT GTTCAGAATT|1421
|TAGGCAACAC|TCAATTTACC|TGCGAAGCAA|TACACCCAGA|CACACCAGTC TTGTATCTCT|1481
|TAAAAGTATG|GATGCTTCAT|CCAAATCGCC|TCACCTACAG|CAGGGAAGTT GACTCATCCA|1541
|AGCATTTTGC|CATGTTTTTT|CTCCCCATGC|CGTACAGGGT|AGCACCTCCT CACCTGCCAA|1601
|TCTTTGCAAT|TTGCTTGACT|CACCTCAGAC|TTTTCATTCA|CAACAGACAG CTTTTAAGGC|1661
|TAACGTCCAG|CTGTATTTAC|TTCTGGCTGT|GCCCGTTTGG|CTGTTTAAGC TGCCAATTGT|1721
|AGCACTCAGC|TACCATCTGA|GGAAGAAAGC|ATTTTGCATC|AGCCTGGAGT GAATCATGAA|1781
|CTTGGATTCA|AGACTGTCTT|TTCTATAGCA|AGTGAGAGCC|ACAAATTCCT CACCCCCTA|1841
|CATTCTAGAA|TGATCTTTTT|CTAGGTAGAT|TGTGTATGTG|TGTGTATGAG AGAGAGAGAG|1901
|AGAGAGAGAG|AGAGAGAGAG|AGAAATTATC|TCAAGCTCCA|GAGGCCTGAT CCAGGATACA|1961
|TCATTTGAAA|CCAACTAATT|TAAAAGCATA|ATAGAGCTAA|TATAT|2006

( 2 ) INFORMATION FOR SEQ ID NO:18:

( i ) SEQUENCE CHARACTERISTICS:
        ( A ) LENGTH: 2024 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 104..1291

( x i ) SEQUENCE DESCRIPTION: SEQ ID NO:18:

| | | | | |
|---|---|---|---|---|
|TAGATGCTGG|GGTTGCAGCC|ACGAGCATAG|ACACGACAGA|CACGGTCCTC GCCATCTTCT|60
|GTTGAGTACT|GGTCGGAACA|AGAGGATCGT|CTGTAGACAG|GAT ATG ATC ATC GTG|115
| | | | |Met Ile Ile Val|
| | | | |1|

| | | | | | | | | | | | | | | | |
|---|---|---|---|---|---|---|---|---|---|---|---|---|---|---|---|---|
|GCG|CAT|GTA|TTA|CTC|ATC|CTT|TTG|GGG|GCC|ACT|GAG|ATA|CTG|CAA|GCT|163
|Ala|His|Val|Leu|Leu|Ile|Leu|Leu|Gly|Ala|Thr|Glu|Ile|Leu|Gln|Ala|
|5| | | | |10| | | | |15| | | | |20|

| | | | | | | | | | | | | | | | |
|---|---|---|---|---|---|---|---|---|---|---|---|---|---|---|---|---|
|GAC|TTA|CTT|CCT|GAT|GAA|AAG|ATT|TCA|CTT|CTC|CCA|CCT|GTC|AAT|TTC|211
|Asp|Leu|Leu|Pro|Asp|Glu|Lys|Ile|Ser|Leu|Leu|Pro|Pro|Val|Asn|Phe|
| | | | |25| | | | |30| | | | |35| |

| | | | | | | | | | | | | | | | |
|---|---|---|---|---|---|---|---|---|---|---|---|---|---|---|---|---|
|ACC|ATT|AAA|GTT|ACT|GGT|TTG|GCT|CAA|GTT|CTT|TTA|CAA|TGG|AAA|CCA|259
|Thr|Ile|Lys|Val|Thr|Gly|Leu|Ala|Gln|Val|Leu|Leu|Gln|Trp|Lys|Pro|
| | | |40| | | | |45| | | | |50| | |

| | | | | | | | | | | | | | | | |
|---|---|---|---|---|---|---|---|---|---|---|---|---|---|---|---|---|
|AAT|CCT|GAT|CAA|GAG|CAA|AGG|AAT|GTT|AAT|CTA|GAA|TAT|CAA|GTG|AAA|307
|Asn|Pro|Asp|Gln|Glu|Gln|Arg|Asn|Val|Asn|Leu|Glu|Tyr|Gln|Val|Lys|
| | |55| | | |60| | | |65| | | | | |

| | | | | | | | | | | | | | | | |
|---|---|---|---|---|---|---|---|---|---|---|---|---|---|---|---|---|
|ATA|AAC|GCT|CCA|AAA|GAA|GAT|GAC|TAT|GAA|ACC|AGA|ATC|ACT|GAA|AGC|355
|Ile|Asn|Ala|Pro|Lys|Glu|Asp|Asp|Tyr|Glu|Thr|Arg|Ile|Thr|Glu|Ser|
|70| | | | |75| | | | |80| | | | | |

| | | | | | | | | | | | | | | | |
|---|---|---|---|---|---|---|---|---|---|---|---|---|---|---|---|---|
|AAA|TGT|GTA|ACC|ATC|CTC|CAC|AAA|GGC|TTT|TCA|GCA|AGT|GTG|CGG|ACC|403
|Lys|Cys|Val|Thr|Ile|Leu|His|Lys|Gly|Phe|Ser|Ala|Ser|Val|Arg|Thr|
|85| | | | |90| | | | |95| | | | |100|

| | | | | | | | | | | | | | | | |
|---|---|---|---|---|---|---|---|---|---|---|---|---|---|---|---|---|
|ATC|CTG|CAG|AAC|GAC|CAC|TCA|CTA|CTG|GCC|AGC|AGC|TGG|GCT|TCT|GCT|451

|     |     |     |     |     | -continued |     |     |     |     |     |     |     |     |     |     |
| --- | --- | --- | --- | --- | --- | --- | --- | --- | --- | --- | --- | --- | --- | --- | --- |
| Ile | Leu | Gln | Asn | Asp 105 | His | Ser | Leu | Leu 110 | Ala | Ser | Ser | Trp | Ala 115 | Ser | Ala |

```
GAA CTT CAT GCC CCA CCA GGG TCT CCT GGA ACC TCA ATT GTG AAT TTA                499
Glu Leu His Ala Pro Pro Gly Ser Pro Gly Thr Ser Ile Val Asn Leu
            120             125             130

ACT TGC ACC ACA AAC ACT ACA GAA GAC AAT TAT TCA CGT TTA AGG TCA                547
Thr Cys Thr Thr Asn Thr Thr Glu Asp Asn Tyr Ser Arg Leu Arg Ser
        135             140             145

TAC CAA GTT TCC CTT CAC TGC ACC TGG CTT GTT GGC ACA GAT GCC CCT                595
Tyr Gln Val Ser Leu His Cys Thr Trp Leu Val Gly Thr Asp Ala Pro
    150             155             160

GAG GAC ACG CAG TAT TTT CTC TAC TAT AGG TAT GGC TCT TGG ACT GAA                643
Glu Asp Thr Gln Tyr Phe Leu Tyr Tyr Arg Tyr Gly Ser Trp Thr Glu
165             170             175             180

GAA TGC CAA GAA TAC AGC AAA GAC ACA CTG GGG AGA AAT ATC GCA TGC                691
Glu Cys Gln Glu Tyr Ser Lys Asp Thr Leu Gly Arg Asn Ile Ala Cys
            185             190             195

TGG TTT CCC AGG ACT TTT ATC CTC AGC AAA GGG CGT GAC TGG CTT GCG                739
Trp Phe Pro Arg Thr Phe Ile Leu Ser Lys Gly Arg Asp Trp Leu Ala
        200             205             210

GTG CTT GTT AAC GGC TCC AGC AAG CAC TCT GCT ATC AGG CCC TTT GAT                787
Val Leu Val Asn Gly Ser Ser Lys His Ser Ala Ile Arg Pro Phe Asp
    215             220             225

CAG CTG TTT GCC CTT CAC GCC ATT GAT CAA ATA AAT CCT CCA CTG AAT                835
Gln Leu Phe Ala Leu His Ala Ile Asp Gln Ile Asn Pro Pro Leu Asn
230             235             240

GTC ACA GCA GAG ATT GAA GGA ACT CGT CTC TCT ATC CAA TGG GAG AAA                883
Val Thr Ala Glu Ile Glu Gly Thr Arg Leu Ser Ile Gln Trp Glu Lys
245             250             255             260

CCA GTG TCT GCT TTT CCA ATC CAT TGC TTT GAT TAT GAA GTA AAA ATA                931
Pro Val Ser Ala Phe Pro Ile His Cys Phe Asp Tyr Glu Val Lys Ile
            265             270             275

CAC AAT ACA AGG AAT GGA TAT TTG CAG ATA GAA AAA TTG ATG ACC AAT                979
His Asn Thr Arg Asn Gly Tyr Leu Gln Ile Glu Lys Leu Met Thr Asn
        280             285             290

GCA TTC ATC TCA ATA ATT GAT GAT CTT TCT AAG TAC GAT GTT CAA GTG               1027
Ala Phe Ile Ser Ile Ile Asp Asp Leu Ser Lys Tyr Asp Val Gln Val
    295             300             305

AGA GCA GCA GTG AGC TCC ATG TGC AGA GAG GCA GGG CTC TGG AGT GAG               1075
Arg Ala Ala Val Ser Ser Met Cys Arg Glu Ala Gly Leu Trp Ser Glu
310             315             320

TGG AGC CAA CCT ATT TAT GTG GGA AAT GAT GAA CAC AAG CCC TTG AGA               1123
Trp Ser Gln Pro Ile Tyr Val Gly Asn Asp Glu His Lys Pro Leu Arg
325             330             335             340

GAG TGG TTT GTC ATT GTG ATT ATG GCA ACC ATC TGC TTC ATC TTG TTA               1171
Glu Trp Phe Val Ile Val Ile Met Ala Thr Ile Cys Phe Ile Leu Leu
            345             350             355

ATT CTC TCG CTT ATC TGT AAA ATA TGT CAT TTA TGG ATC AAG TTG TTT               1219
Ile Leu Ser Leu Ile Cys Lys Ile Cys His Leu Trp Ile Lys Leu Phe
        360             365             370

CCA CCA ATT CCA GCA CCA AAA AGT AAT ATC AAA GAT CTC TTT GTA ACC               1267
Pro Pro Ile Pro Ala Pro Lys Ser Asn Ile Lys Asp Leu Phe Val Thr
    375             380             385

ACT AAC TAT GAG AAA GCT GGA ATT TAAATTCAAG CATGTTTTAA CTTTTGGTTT              1321
Thr Asn Tyr Glu Lys Ala Gly Ile
390             395

AAGGTACTTG GGTGTACCTG GCAGTGTTGT AAGCTCTTTA CATTAATTAA TTAACTCTCT             1381

AGGTACTGTT ATCTTCATTT TATAAACAAG GCAGCTGAAG TTGAGAGAAA TAAGTAACCT             1441
```

| | | | | | |
|---|---|---|---|---|---|
| GTCCTAGGTC | ACACAATTAG | GAAATGACAG | ATCTGGCAGT | CTATTTCCAG | GCAGTCTATT | 1501 |
| TCCACGAGGT | CATGAGTGCG | AAAGAGGGAC | TAGGGAAGA | ATGATTAACT | CCAGGGAGCT | 1561 |
| GACTTTTCTA | GTGTGCTTAC | CTGTTTTGCA | TCTCTCAAGG | ATGTGCCATG | AAGCTGTAGC | 1621 |
| CAGGTGGAAT | TGTACCACAG | CCCTGACATG | AACACCTGAT | GGCAGCTGCT | GGGTTGGAGC | 1681 |
| CTAGACAAAA | ACATGAAGAA | CCATGGCTGC | TGCCTGAGCC | CATCGTGCTG | TAATTATAGA | 1741 |
| AAACCTTCTA | AGGGAAGAAT | ATGCTGATAT | TTTTCAGATA | AGTACCCCTT | TTATAAAAAT | 1801 |
| CCTCCAAGTT | AGCCCTCGAT | TTTCCATGTA | AGGAAACAGA | GGCTTTGAGA | TAATGTCTGT | 1861 |
| CTCCTAAGGG | ACAAAGCCAG | GACTTGATCC | TGTCTTAAAA | ATGCAAAATG | TAGTACTTCT | 1921 |
| TCCATCAAAG | GTAGACATGC | ACTAAGGGAC | AGGTTTTGGC | TTGGTATCAG | AATACATTTT | 1981 |
| TAAAAGCTGT | GTAAGAATTG | AACGGGCTGT | ACTAGGGGGT | ATA | | 2024 |

1. A substantially purified murine interleukin 5 receptor wherein the amino acid sequence comprises the sequence described in SEQ ID NO. 5.

2. A substantially purified murine interleukin 5 receptor wherein the amino acid sequence consists of the sequence described in SEQ ID NO. 6.

3. A substantially purified murine secretory interleukin 5 receptor wherein the amino acid sequence comprises the sequence described in SEQ ID NO. 7.

4. A substantially purified murine secretory interleukin 5 receptor wherein the amino acid sequence consists of the sequence described in SEQ ID NO. 8.

5. A substantially purified interleukin 5 receptor wherein the amino acid sequence is selected from the group consisting of SEQ ID NO. 5, SEQ ID NO, 6, SEQ ID NO. 7, and SEQ ID NO. 8.

* * * * *